United States Patent
Li et al.

(10) Patent No.: US 6,369,220 B1
(45) Date of Patent: Apr. 9, 2002

(54) METHOD OF PREPARING ENANTIOMERICALLY-ENRICHED TETRAHYDROBENZOTHIEPINE OXIDES

(76) Inventors: Jinglin (James T.) Li, 62-13 Ravens Crest Dr., Plainsboro, NJ (US) 08536; Ching-Cheng Wang, 2470 Maple Crossing Dr., Wildwood, MO (US) 63011; David B. Reitz, 14814 Pleasant Ridge Ct., Chesterfield, MO (US) 63017; Victor Snieckus, Dept. of Chemistry, Queen's University Kingston, Ontario (CA), K7L 3N6; Horng-Chih Huang, 15481 Duxbury Way, Chesterfield, MO (US) 63017; Andrew J. Carpenter, Five Moore Dr., Research Triangle Park, NC (US) 27709-3398

( * ) Notice: Subject to any disclaimer, the term of this patent is extended or adjusted under 35 U.S.C. 154(b) by 0 days.

(21) Appl. No.: 09/581,897

(22) PCT Filed: Dec. 16, 1998

(86) PCT No.: PCT/US98/26216

§ 371 Date: Oct. 2, 2000

§ 102(e) Date: Oct. 2, 2000

(87) PCT Pub. No.: WO99/32478

PCT Pub. Date: Jul. 1, 1999

Related U.S. Application Data

(60) Provisional application No. 60/068,170, filed on Dec. 19, 1997.

(51) Int. Cl.[7] .................... C07D 245/02; C07D 337/16; A61K 31/55
(52) U.S. Cl. ................ 540/473; 549/9; 514/211.01
(58) Field of Search ............................ 549/9; 540/473; 514/211.01

(56) References Cited

U.S. PATENT DOCUMENTS 5,559,017 A  9/1996  Patel et al.

FOREIGN PATENT DOCUMENTS

| CA | 2068231 A1 | 11/1992 |
| JP | 59-144777 | 8/1984 |
| WO | WO96 08484 A | 3/1996 |
| WO | WO97 33882 A | 9/1997 |

OTHER PUBLICATIONS

Davis et al., "Chemistry of Oxaziridines," *J. Am. Chem. Soc.*, 1992, 114(4), 1428–1437.

Palucki et al., Asymmetric Oxidation of Sulfides with $H_2O_2$ Catalyzed by (salen)Mn(III) Complexes, *Tetrahedron Letters*, 1992, 33(47), 7111–7114.

Sasaki et al., "Preparation and Characterization of Optically Active Quadridentate Schiff Base–Titanium(IV) Complexes . . . ," *Bull. Chem. Soc. Japan*, 1991, 64, 1318–1324.

Silverman, R.B., "The Organic Chemistry of Drug Design and Drug Action," *Academic Press*, 1992, pp. 76–82.

Stredonsky, E.R., "Interaction of Bile acids and cholesterol with nonsystemic agents having hypocholesterolemic properties," *Biochemica et Biophysica Acta*, 1210 (1994) 255–287.

Yamada et al., "Asymmetric Reduction of a 1,5–Benzothiazepine Derivative with Sodium Borohydride . . . ," *J. Org. Chem.* 1995, 61 (24) 8586–8590.

Zhao et al., "Asymmetric Oxidation of Sulfides Mediated by Chiral Titanium Complexes: Mechanistic and Synthetic Aspects," *Tetrahedron*, 1987, 43(21), 5135–5144.

*Primary Examiner*—Floyd D. Higel
*Assistant Examiner*—Ebenezer Sackey
(74) *Attorney, Agent, or Firm*—Banner & Witcoff Ltd.

(57) ABSTRACT

A process for preparing enantiomerically enriched tetrahydrobenzothipeine oxides comprises cyclizing an enantiomerically enriched aryl-3-propanalsulfoxide wherein the sulfur atom of the aryl-3-propanalsulfoxide is a chiral center.

66 Claims, 2 Drawing Sheets

METHOD OF PREPARING ENANTIOMERICALLY-ENRICHED TETRAHYDROBENZOTHIEPINE OXIDES

This application is a 371 of PCT/US98/26216 filed Dec. 16, 1998 which claims the benefit of priority of U.S. Provisional Application Serial No. 60/068,170, filed Dec. 19, 1997, the entire contents of which are herein incorporated by reference.

BACKGROUND OF THE INVENTION

1. Field of the Invention

The present invention relates to a novel method of preparing enantiomerically-enriched tetrahydrobenzothiepine oxides.

2. Description of Related Art

It is well established that agents which inhibit the transport of bile acids across the ileum can also cause a decrease in the level of cholesterol in blood serum. Stedronski, in "Interaction of bile acids and cholesterol with nonsystemic agents having hypocholesterolemic properties," Biochimica et Biophysica Acta, 1210 (1994) 255–287, discusses biochemistry, physiology, and known active agents affecting bile acids and cholesterol.

A class of ileal bile acid transport-inhibiting compounds which was recently discovered to be useful for influencing the level of blood serum cholesterol is tetrahydrobenzothiepine-1,1-dioxides (THBDO compounds). (U.S. patent application Ser. No. 08/816,065= WO96/08484).

Some classes of compounds show enhanced potency as pharmaceutical therapeutics after they have been enantiomerically-enriched (see, for example, Richard B. Silverman, *The Organic Chemistry of Drug Design and Drug Action*, Academic Press, 1992, pp. 76–82). Therefore, THBDO compounds that have been enantiomerically-enriched are of particular interest.

A class of chemistry useful as intermediates in the preparation of racemic THBDO compounds is tetrahydrobenzothiepine-1-oxides (THBO compounds). THBDO compounds and THBO compounds possess chemical structures in which a phenyl ring is fused to a seven-member ring. A method of preparing enantiomerically-enriched samples of another phenyl/seven-member fused ring system, the benzothiazepines, is described by Higashikawa (JP 59144777), where racemic benzothiazepine derivatives are optically resolved on a chromatographic column containing chiral crown ethers as a stationary phase. Although optical resolution is achieved, the Higashikawa method is limited to producing only small quantities of the enantiomerically-enriched benzothiazepine derivatives.

Giordano (CA 2068231) reports the cyclization of (2S, 3S)-aminophenylthiopropionates in the presence of a phosphonic acid to produce (2S,3S)-benzothiazepin-4-ones. However, that preparation is constrained by the need to use enantiomerically-enriched starting materials rather than racemic starting materials. In addition, the Giordano method controls the stereochemistry of the seven-member ring of the benzothiazepin-4-one only at the 2- and 3-positions. The 4-and 5-positions of the seven-member ring of the benzothiazepin-4-one are not asymmetric centers, and the stereochemistry at these sites therefore cannot be controlled by the Giordano method.

A method by which enantiomerically-enriched 1,5-benzothiazepin-3-hydroxy-4(5H)-one compounds have been produced is through the asymmetric reduction of 1,5-benzothiazepin-3,4(2H,5H)-dione compounds, reported by Yamada, et al. (J. Org. Chem. 1996, 61 (24), 8586–8590). The product is obtained by treating the racemic 1,5-benzothiazepin-3,4(2H,5H)-dione with the reaction product of an optically active alpha-amino acid and a reducing agent, for example sodium borohydride. Although a product with high optical purity was achieved, the method is limited by the use of a relatively expensive chemical reduction step.

The microbial reduction of racemic 1,5-benzothiazepin-3,4(2H,5H)-dione compounds to produce enantiomerically-enriched 1,5-benzothiazepin-3-hydroxy-4(5H)-one compounds is reported by Patel et al., U.S. Pat. No. 5,559,017. This method is limited by the inherent problems of maintaining a viable and pure bacterial culture of the appropriate species and variety. In addition, that method is limited in scale, producing only microgram quantities of the desired product.

Until now, there have been no reported processes for preparing enantiomerically-enriched THBDO compounds or enantiomerically-enriched THBO compounds. Furthermore, there have been no reported processes for controlling the stereochemistry at the 4- and 5-positions of the seven-member rings of THBDO compounds or THBO compounds.

SUMMARY OF THE INVENTION

A convenient and cost-effective method for preparing enantiomerically-enriched THBDO compounds and intermediates in the preparation thereof is of great importance and utility. In response to the need therefor, the present inventors have developed a method for preparing enantiomerically-enriched tetrahydrobenzothiepine-1-oxides or enantiomerically-enriched tetrahydrobenzothiepine-1,1-dioxides with chiral centers at the 4- and 5-positions of the seven-member ring.

Accordingly, among its various aspects, the present invention provides a method of preparing an enantiomerically-enriched tetrahydrobenzothiepine-1-oxide having the formula (I):

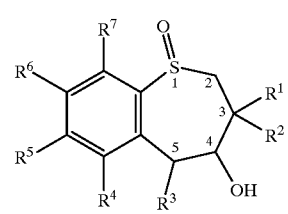

(I)

wherein:

$R^1$ and $R^2$ are independently selected from among H, alkyl, alkenyl, alkynyl, cycloalkyl, aryl and heteroaryl;

$R^3$ is selected from the group consisting of H, alkyl, alkenyl, alkynyl, aryl, cycloalkyl, heterocycle, quaternary heterocycle, $OR^{24}$, $SR^{15}$, $S(O)R^{15}$, $SO_2R^{15}$, and $SO_3R^{15}$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{19}$, $NR^{19}R^{20}$, $SR^{19}$, $S(O)R^{19}$, $SO_2R^{19}$, $SO_3R^{19}$, $NR^{19}OR^{20}$, $NR^{19}NR^{20}R^{21}$, $NO_2$, $CO_2R^{19}$, CN, OM, $SO_2OM$, $SO_2NR^{19}R^{20}$, C(O)

$NR^{19}R^{20}$, $C(O)OM$, $COR^{19}$, $P(O)R^{19}R^{20}$, $P^+R^{19}R^{20}R^{21}A^-$, $P(OR^{19})OR^{20}$, $S^+R^{19}R^{20}A^{13}$, and $N^+R^{15}R^{17}R^{18}A^-$, wherein:

$A^-$ is a pharmaceutically acceptable anion and M is a pharmaceutically acceptable cation;

said alkyl, alkenyl, alkynyl, polyalkyl, polyether, aryl, haloalkyl, cycloalkyl, and heterocycle can be further substituted with one or more substituent groups selected from the group consisting of $OR^{13}$, $NR^{13}R^{14}$, $SR^{13}$, $S(O)R^{13}$, $SO_2R^{13}$, $SO_3R^{13}$, $CO_2R^{13}$, CN, oxo, $CONR^{13}R^{14}$, $N^+R^{13}R^{14}R^{15}A-$, alkyl, alkenyl, alkynyl, aryl, cycloalkyl, heterocycle, arylalkyl, quaternary heterocycle, quaternary heteroaryl, $P(O)R^{13}R^{14}$, $P^+R^{13}R^{14}R^{15}A^-$, and $P(O)(OR^{13})OR^{14}$, and wherein said alkyl, alkenyl, alkynyl, polyalkyl, polyether, aryl, haloalkyl, cycloalkyl, and heterocycle can optionally have one or more carbons replaced by O, $NR^{13}$, $N^+R^{13}R^{14}A-$, S, SO, $SO^2$, $S^+R^{13}A-$, $PR^{13}$, $P(O)R^{13}$, $P^+R^{13}R^{14}A-$, or phenylene;

$R^{19}$, $R^{20}$, and $R^{21}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, polyether, alkylarylalkyl, alkylheteroarylalkyl, alkylheterocyclealkyl, heterocyclealkyl, heteroarylalkyl, quaternary heterocyclealkyl, alkylammoniumalkyl, carboxyalkylaminocarbonylalkyl, and quaternary heteroarylalkyl, wherein alkyl, alkenyl, alkynyl, arylalkyl, heterocycle, and polyalkyl optionally have one or more carbons replaced by O, $NR^{15}$, $N^+R^{15}R^{16}A-$, S, SO, $SO_2$, $S^+R^{15}A^-$, $PR^{15}$, $P^+R^{15}R^{16}A-$, $P(O)R^{15}$, phenylene, carbohydrate, amino acid, peptide, or polypeptide, and $R^{19}$, $R^{20}$, and $R^{21}$ are optionally substituted with one or more groups selected from the group consisting of hydroxy, amino, sulfo, carboxy, sulfoalkyl, carboxyalkyl, sulfoalkyl, alkyl, heterocycle, heteroaryl, quaternary heterocyclealkyl, quaternary heteroarylalkyl, guanidinyl, quaternary heterocycle, quaternary heteroaryl, $OR^{15}$, $NR^{15}R^{16}$, $N^+R^{15}R^{17}R^{18}A^-$, $SR^{15}$, $S(O)R^{15}$, $SO_2R^{15}$, $SO_3R^{15}$, oxo, $CO_2R^{15}$, CN, halogen, $CONR^{15}R^6$, $S_2OM$, $SO_2NR^{15}R^{16}$, $PO(OR^{22})OR^{23}$, $P^+R^{15}R^{16}R^{17}A-$, $S^+R^{15}R^{16}A-$, and $C(O)OM$, wherein $R^{22}$ and $R^{23}$ are independently selected from the substituents constituting $R^{15}$ and M, or $R^{20}$ and $R^{21}$, together with the nitrogen atom to which they are attached, form a cyclic ring;

$R^{24}$ is selected from the group consisting of alkyl, alkenyl, alkynyl, cycloalkyl, aryl, acyl, heterocycle, ammoniumalkyl, alkylammoniumalkyl, and arylalkyl;

$R^{13}$ and $R^{14}$ are independently selected from the group consisting of hydrogen and alkyl;

$R^{15}$ and $R^{16}$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboalkylamino, heteroarylalkyl, heterocyclealkyl, and alkylammoniumalkyl; and $R^{17}$ and $R^{18}$ are independently selected from the group consisting of H, alkyl, alkenyl, alkynyl, aryl, arylalkyl, alkenylalkyl, alkynylalkyl, carboxyalkyl, carboalkoxyalkyl, cycloalkyl, cyanoalkyl, $OR^{15}$, $NR^{15}R^{16}$, $SR^{15}$, $S(O)R^{15}$, $SO_2R^{15}$, $SO_3R^{15}$, $CO_3R^{15}$, CN, halogen, oxo, and $CONR^{15}R^{16}$, wherein $R^{15}$ and $R^{16}$ are as defined above, or $R^{17}$ and $R^{18}$ together with the nitrogen or carbon atom to which they are attached form a cyclic ring; and $R^4$, $R^5$, $R^6$, and $R^7$ are independently selected from among H, alkyl, alkenyl, alkynyl, cycloalkyl, aryl, heteroaryl, halo, alkoxy, aryloxy, $-NO_2$, and $-NR^9R^{10}$; R and $R^{10}$ are independently selected from among H, alkyl, alkenyl, alkynyl, cycloalkyl, aryl, heteroaryl, butoxycarbonyl, and carbobenzyloxy;

$R^3$ and the hydroxyl at the 4-position of the enantiomerically-enriched tetrahydrobenzothiepine-1-oxide are in a syn-conformation with respect to each other; wherein alkyl, alkenyl, alkynyl, cycloalkyl, aryl, and heteroaryl can be optionally substituted with one or more moieties selected from among alkyl, alkenyl, alkynyl, cycloalkyl, aryl, heteroaryl, alkoxy, aryloxy, $-NO_2$, and halo; and the sulfur at the 1-position of the seven-member ring and the carbon atoms at the 4-position and the 5-position of the seven member ring are chiral centers.

The method comprises cyclizing an enantiomerically-enriched aryl-3-propanalsulfoxide having the formula (II):

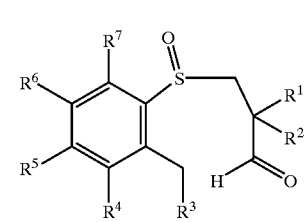

(II)

wherein $R^1$, $R^2$, $R^3$, $R^4$, $R^5$, $R^6$, and $R^7$ are as described above, and wherein the sulfur is a chiral center, to form the enantiomerically-enriched tetrahydrobenzothiepine-1-oxide.

In another embodiment, the present invention also provides a method of preparing an enantiomerically-enriched tetrahydrobenzothiepine-1-oxide having the formula (I), wherein the method comprises oxidizing an aryl-3-hydroxypropylsulfide having the formula (IV):

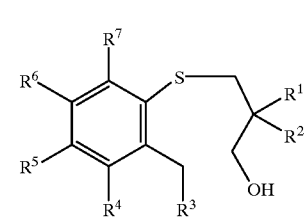

(IV)

wherein $R^1$, $R^2$, $R^3$, $R^4$, $R^5$, $R^6$, and $R^7$ are as described above, and wherein the oxidation is performed under enantioselective oxidation conditions to produce an enantionmerically-enriched aryl-3-hydroxypropylsulfoxide having formula (III):

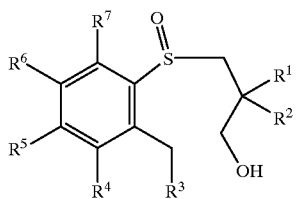

(III)

wherein $R^1$, $R^2$, $R^3$, $R^4$, $R^5$, $R^6$, and $R^7$ are as described above, and the sulfur is a chiral center; oxidizing the 3-hydroxyl group of the enantionmerically-enriched aryl-3-hydroxypropylsulfoxide to produce an enantiomerically-enriched aryl-3-propanalsulfoxide having the formula (II); and cyclizing the enantionmerically-enriched aryl-3-propanalsulfoxide to form the enantiomerically-enriched tetrahydrobenzothiepine-1-oxide.

In yet another embodiment, the present invention also provides a method of preparing an enantiomerically-enriched tetrahydrobenzothiepine-1,1-dioxide having the formula (VII):

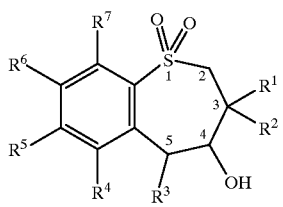

(VII)

wherein $R^1$, $R^2$, $R^3$, $R^4$, $R^5$, $R^6$, and $R^7$ are as described above, $R^3$ the hydroxyl at the 4-position of the enantiomerically-enriched tetrahydrobenzothiepine-1-oxide are in a syn-conformation with respect to each other, and the carbons at the 4-position and the 5-position of the seven member ring are chiral centers. The method comprises oxidizing an aryl-3-hydroxypropylsulfide having the formula (IV) under enantioselective oxidation conditions to produce an enantiomerically-enriched aryl-3-hydroxypropylsulfoxide having the formula (III) and having a chiral center at the sulfur; oxidizing the enantiomerically-enriched aryl-3-hydroxypropyl-sulfoxide to produce an enantiomerically-enriched aryl-3-propanalsulfoxide having the formula (II); cyclizing the enantiomerically-enriched aryl-3-propanalsulfoxide to form an enantiomerically-enriched tetrahydrobenzothiepine-1-oxide having the formula (I) and having chiral centers at the sulfur at the 1-position of the seven-member ring and at the carbons at the 4-position and the 5-position of the seven member; and oxidizing the enantiomerically-enriched tetrahydrobenzothiepine-1-oxide to the enantiomerically-enriched tetrahydrobenzothiepine-1,1-dioxide.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

In still another embodiment, the present invention provides an ileal bile acid transport-inhibiting compound (IBAT inhibitors) useful for the prophylaxis or treatment of cardiovascular disease including hypercholesterolemia and atherosclerosis, said IBAT inhibitor compound having the structure of formula ((4R,5R)-XXVII):

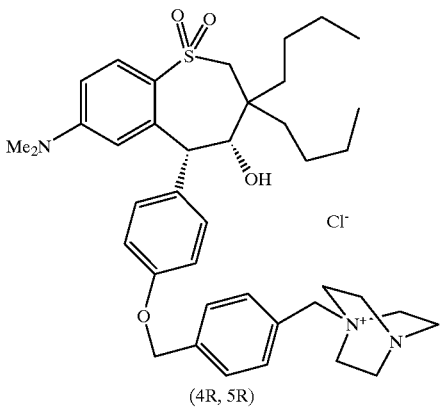

((4R, 5R) - XXVII)

(4R, 5R)

In still another embodiment, the present invention provides an ileal bile acid transport-inhibiting compound (IBAT inhibitors) useful for the prophylaxis or treatment of cardiovascular disease including hypercholesterolemia and atherosclerosis, said IBAT inhibitor compound having the structure of formula ((4S,5S)-XXVII):

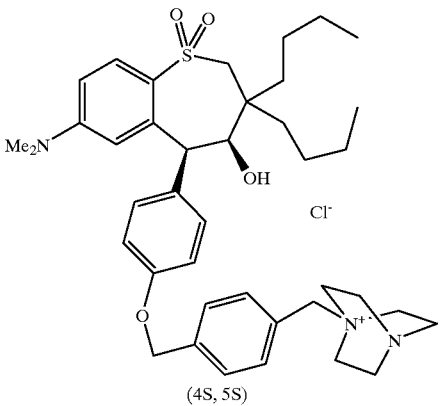

((4S, 5S) - XXVII)

(4S, 5S)

BRIEF DESCRIPTION OF THE DRAWINGS

FIG. I is a reaction scheme exemplifying the preparation of an enantiomerically enriched tetrahydrobenzothiepine-1,1-dioxide.

FIG. II is a reaction scheme exemplifying the preparation of a cyclic sulfate.

DETAILED DESCRIPTION OF THE INVENTION

Figure 1:
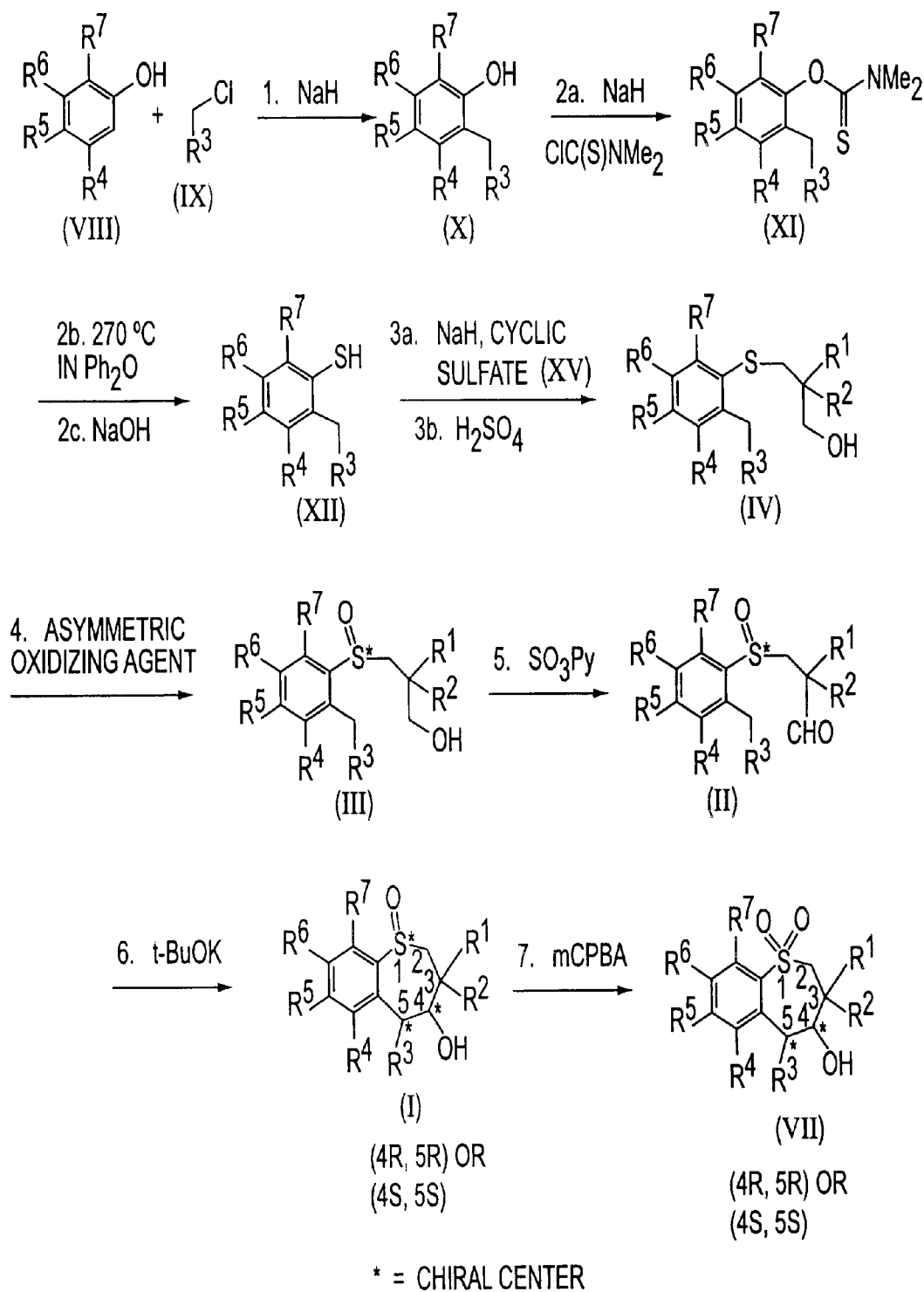
Figure 2:
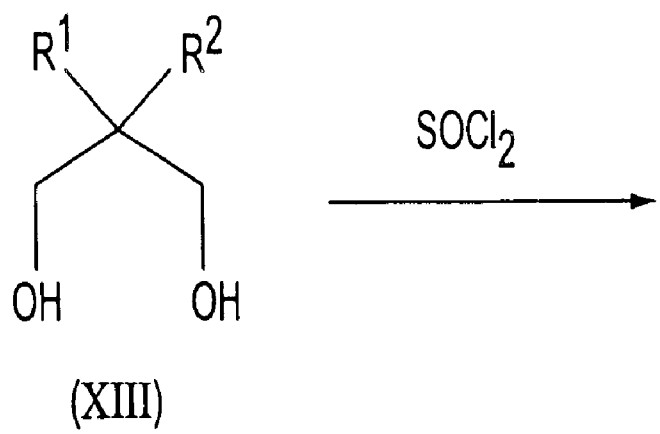
Figure 2:
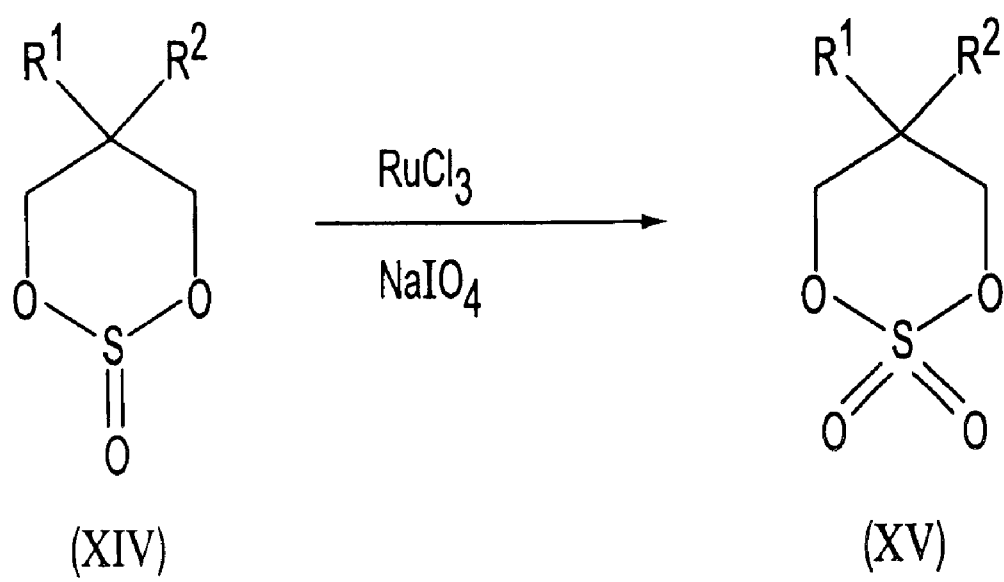

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

In order to aid the reader in understanding the following detailed description, the following definitions are provided:

"Alkyl," "alkenyl," and "alkynyl," unless otherwise noted, are each straight chain, branched chain, or cyclic hydrocarbons or substituted hydrocarbons of from one to about twenty carbons for alkyl, or from two to about twenty carbons for alkenyl, or from two to about twenty carbons for alkynyl. Alkyl can therefore mean, for example, methyl, ethyl, propyl, butyl, pentyl, hexyl, methylcyclopentyl, and isomers thereof. Alkenyl can mean, for example, ethenyl, propenyl, butenyl, pentenyl, or hexenyl, and isomers thereof. Alkynyl can mean, for example, ethyne, propyne, butyne, pentyne, or hexyne and isomers thereof. The alkyl, alkenyl, or alkynyl group can optionally have one or more hydrogen atom substituted with a substituent group. Such substituent groups can include, for example, cycloalkyl, aryl, heteroaryl, halo, alkoxy, hydroxy, aryloxy, —$NO_2$, amino, or alkylamino.

"Aryl" means a fully unsaturated mono- or multi-ring carbocycle, including, but not limited to, substituted or unsubstituted phenyl, naphthyl, or anthracenyl.

"Heteroaryl" means a fully unsaturated heterocycle.

"Heterocycle" means a saturated or unsaturated mono- or multi-ring carbocycle wherein one or more carbon atoms can be replaced by N, S, P, or O. This includes, for example, the following structures:

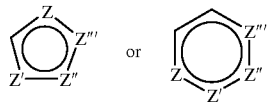

wherein Z, Z', Z", or Z'" is C, S, P, O, or N, with the proviso that one of Z, Z', Z", or Z'" is other than carbon, but is not O or S when attached to another Z atom by a double bond or when attached to another O or S atom. Furthermore, the optional substituents are understood to be attached to Z, Z', Z", or Z'" only when each is C.

In either "heterocycle" or "heteroaryl," the point of attachment to the molecule of interest can be at the heteroatom or elsewhere within the ring.

"Halogen" means a fluoro, chloro, bromo, or iodo group.

"Cycloalkyl" means a mono- or multi-ringed carbocycle wherein each ring contains three to ten carbon atoms, and wherein any ring can contain one or more double or triple bonds, but is not fully unsaturated.

"Alkoxy" means an alkyl group attached by a single bond to an oxygen. This includes, for example, methoxy, ethoxy, propoxy, butoxy, and isomers thereof.

"Aryloxy" means an aryl group attached by a single bond to an oxygen. This includes, for example, phenoxy.

"Carboalkyl" means an alkyl group attached by a single bond to a carbonyl group. This includes, for example, —$COCH_3$, —$COCH_2CH_3$, —$COCH_2CH_2CH_3$, and —$COCH_2CH_2CH_3$, and isomers thereof.

"Chiral (salen)metal complex" means an optically active quadridentate Schiff base-metal complex. This includes, for example, (S,S)-(+)-N,N'-bis(3,5-di-tert-butylsalicyclidene)-1,2-cyclohexanediaminomanganese (III) chloride, or (R,R)-(+)-N,N'-bis(3,5-di-tert-butylsalicyclidene)-1,2-diphenylethylenediaminomanganese (III) chloride.

When used in combination, for example "alkylaryl" or "arylalkyl," the individual terms have the meaning indicated above.

"Enantioselective oxidation conditions" means conditions conducive to favoring as oxidation products one enantiomer or set of diastereomers over another enantiomer or set of diastereomers.

"Chiral" means the inability of a molecule to be superimposed on its mirror image. A chiral center in a molecule is an atom which has a tetrahedral, noninvertable geometry and for which each apex of the tetrahedron is different from the other apices. Chiral centers include, for example, carbon atoms having four different substituents bonded to it. Another example of a chiral center is a sulfur atom in a sulfoxide moiety which has bonded to the sulfur an oxygen and two other different substituents.

"Enantiomerically-enriched" means that one enantiomer or set of diastereomers preponderates over the complementary enantiomer or set of diastereomers. Enantiomeric enrichment of a compound is typically determined by separating a mixture of a first enantiomer and a second enantiomer, for example by chiral chromatography, integrating the areas of the two enantiomer peaks, summing the areas, dividing the individual area of each enantiomer peak by the summed area of the two peaks, and expressing the dividends as percents of the total mixture of the two enantiomers. If the first enantiomer preponderates over the second enantiomer, the percent of the second enantiomer is subtracted from the percent of the first enantiomer and the resulting difference is expressed as percent enantiomeric enrichment (P e.e.) of the first enantiomer. Enantiomeric enrichment can be from about 1 to about 100% e.e., preferably from about 10 to about 100% e.e., and more from about 20 to about 100% e.e., and still more preferably from about 50 to about 100% e.e.

"Asymmetric oxidizing agent" means an oxidizing agent that induces a chiral center at the site of oxidation to produce, for example, a chiral sulfoxide.

"NMR" means nuclear magnetic resonance spectroscopy.

"GC" means gas chromatography.

"HPLC" means high pressure liquid chromatography.

"MS" means mass spectrometry.

Overview of Preparative Methods

Among its various embodiments, the present invention provides a method of preparing an enantiomerically-enriched tetrahydrobenzothiepine-1-oxide having the formula (I):

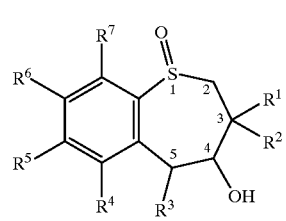

wherein:

$R^1$ and $R^2$ are independently selected from among H, alkyl, alkenyl, alkynyl, cycloalkyl, aryl and heteroaryl;

R³ is selected from the group consisting of H, alkyl, alkenyl, alkynyl, aryl, cycloalkyl, heterocycle, quaternary heterocycle, $OR^{24}$, $SR^{15}$, $S(O)R^{15}$, $SO^2R_{15}$, and $SO_3R^{15}$, wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{19}$, $NR^{19}R^{20}$, $SR^{19}$, $S(O)R^{19}$, $SO_2R^{19}$, $SO_3R^{19}$, $NR^{19}OR^{20}$, $NR^{19}NR^{20}R^{21}$, $NO_2$, $CO_2R^{19}$, CN, OM, $SO_2OM$, $SO_2NR^{19}R^{20}$, $C(O)NR^{19}R^{20}$, $C(O)OM$, $COR^{19}$, $P(O)R^{19}R^{20}$, $P^+R^{19}R^{20}r^{21}A^-$, $P(OR^{19})OR^{20}$, $S^+R^{19}R^{20}A^-$, and $N^+R^{15}R^{17}R^{18}A^-$, wherein:
A⁻ a pharmaceutically acceptable anion and M is a pharmaceutically acceptable cation;

said alkyl, alkenyl, alkynyl, polyalkyl, polyether, aryl, haloalkyl, cycloalkyl, and heterocycle can be further substituted with one or more substituent groups selected from the group consisting of $OR^{13}$, $NR^{13}R^{14}$, $SR^{13}$, $S(O)R^{13}$, $SO^2R^{13}$, $SO_3R^{13}$, $CO_2R^{13}$, CN, oxo, $CONR^{13}R^{14}$, $N^+R^{13}R^{14}R^{15}A$—, alkyl, alkenyl, alkynyl, aryl, cycloalkyl, heterocycle, arylalkyl, quaternary heterocycle, quaternary heteroaryl, $P(O)R^{13}R^{14}$, $P^+R^{13}R^{14}R^{15}A^-$, and $P(O)(OR^{13})OR^{14}$, and wherein said alkyl, alkenyl, alkynyl, polyalkyl, polyether, aryl, haloalkyl, cycloalkyl, and heterocycle can optionally have one or more carbons replaced by O, $NR^{13}$, $N^+R^{13}R^{14}A$—, S, SO, $SO_2$, $S^+R^{13}A$-, $PR^{13}$, $P(O)R^{13}$, $P^+R^{13}R^{14}A$—, or phenylene;

$R^{19}$, $R^{20}$, and $R^{21}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, polyether, alkylarylalkyl, alkylheteroarylalkyl, alkylheterocyclealkyl, heterocyclealkyl, heteroarylalkyl, quaternary heterocyclealkyl, alkylammoniumalkyl, carboxyalkylaminocarbonylalkyl, and quaternary heteroarylalkyl, wherein alkyl, alkenyl, alkynyl, arylalkyl, heterocycle, and polyalkyl optionally have one or more carbons replaced by O, $NR^{15}$, $N^+R^{15}R^{16}A$—, S, SO, $SO_2$, $S^+R^{15}A^-$, $PR^{15}$, $P^+R^{15}R^{16}A$—, $P(O)R^{15}$, phenylene, carbohydrate, amino acid, peptide, or polypeptide, and $R^{19}$, $R^{20}$, and $R^{21}$ are optionally substituted with one or more groups selected from the group consisting of hydroxy, amino, sulfo, carboxy, sulfoalkyl, carboxyalkyl, sulfoalkyl, alkyl, heterocycle, heteroaryl, quaternary heterocyclealkyl, quaternary heteroarylalkyl, guanidinyl, quaternary heterocycle, quaternary heteroaryl, $OR^{15}$ $NR^{15}R^{16}$, $N^+R^{15}R^{17}R^{18}A^-$, $SR^{15}$, $S(O)R^{15}$, $SO_2R^{15}$, $SO_3R^{15}$, oxo, $CO_2R^{15}$, CN, halogen, $CONR^{15}R^{16}$, $SO_2OM$, $SO_2NR^{15}R^{16}$, $PO(OR^{22})OR^{23}$, $P^+R^{15}R^{16}R^{17}A$—, $S^+R^{15}R^{16}A$—, and C(O)OM, wherein $R^{22}$ and $R_{23}$ are independently selected from the substituents constituting $R^{15}$ and M, or $R^{20}$ and $R^{21}$, together with the nitrogen atom to which they are attached, form a cyclic ring;

$R^{24}$ is selected from the group consisting of alkyl, alkenyl, alkynyl, cycloalkyl, aryl, acyl, heterocycle, ammoniumalkyl, alkylammoniumalkyl, and arylalkyl;

$R^{13}$ and $R^{14}$ are independently selected from the group consisting of hydrogen and alkyl;

$R^{15}$ and $R^{16}$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboalkylamino, heteroarylalkyl, heterocyclealkyl, and alkylammoniumalkyl; and $R^{17}$ and $R^{18}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^{15}$, $NR^{15}R^{16}$, $SR^{15}$, $S(O)R^{15}$, $SO_2R^{15}$, $SO_3R^{15}$, $CO_3R^{15}$, CN, halogen, oxo, and $CONR^{15}R^{16}$, wherein $R^{15}$ and $R^{16}$ are as defined above, or $R^{17}$ and $R^{18}$ together with the nitrogen or carbon atom to which they are attached form a cyclic ring; and $R^4$, $R^5$, $R^6$, and $R^7$ are independently selected from among H, alkyl, alkenyl, alkynyl, cycloalkyl, aryl, heteroaryl, halo, alkoxy, aryloxy, —$NO_2$, and —$NR^9R^{10}$; $R^9$ and $R_{10}$ are independently selected from among H, alkyl, alkenyl, alkynyl, cycloalkyl, aryl, heteroaryl, butoxycarbonyl, and carbobenzyloxy;

$R^3$ and the hydroxyl at the 4-position of the enantiomerically-enriched tetrahydrobenzothiepine-1-oxide are in a syn-conformation with respect to each other; wherein alkyl, alkenyl, alkynyl, cycloalkyl, aryl, and heteroaryl can be optionally substituted with one or more moieties selected from among alkyl, alkenyl, alkynyl, cycloalkyl, aryl, heteroaryl, alkoxy, aryloxy, —$NO_2$, and halo; and the sulfur at the 1-position of the seven-member ring and the carbon atoms at the 4-position and the 5-position of the seven member ring are chiral centers.

Preferably, the enantiomerically-enriched tetrahydrobenzothiepine-1-oxide of formula (I) has the structure shown in formula ((4R,5R)-XXVII), ((4S,5S)-XXVII), ((4R,5R)-XXVI), or ((4S,5S)-XXVI).

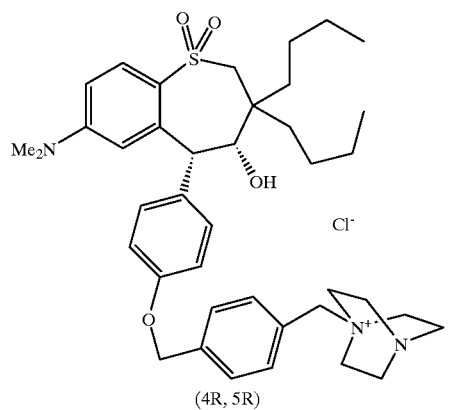

((4R, 5R) - XXVII)

(4R, 5R)

((4S, 5S) - XXVII)

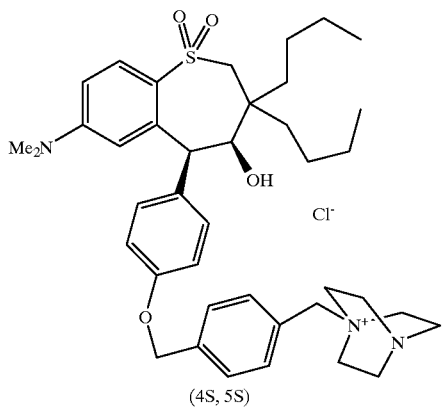

(4S, 5S)

((4R, 5R) - XXVI)

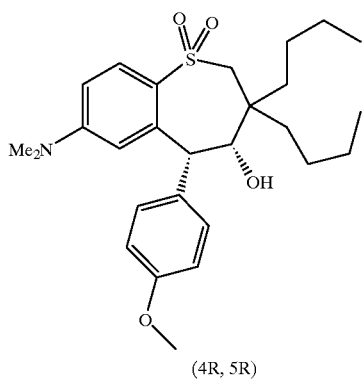

(4R, 5R)

((4R, 5R) - XXVI)

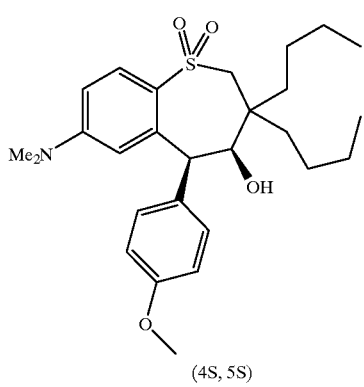

(4S, 5S)

Preferably, $R^1$ and $R^2$ are both alkyl. More preferably, both $R^1$ and $R^2$ are butyl. In another preferred embodiment, one of $R^1$ and $R^2$ is ethyl and the other of $R^1$ and $R^2$ is butyl. Preferably, $R^4$, $R^5$, $R^6$, and $R^7$ are independently selected from among H, —$NO_2$, and —$NR^9R^{10}$. More preferably, $R^4$, $R^6$, and $R^7$ are each H and $R^5$ is —$NO_2$ or —$NR^9N^{10}$. Still more preferably, $R^4$, $R^6$, and $R^7$ are each H and $R^5$ is dimethylamino. The method comprises cyclizing an enantiomerically-enriched aryl-3-propanalsulfoxide having the formula (II):

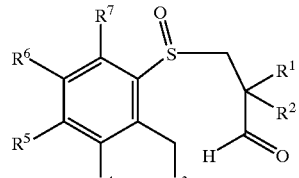

(II)

wherein $R^1$, $R^2$, $R^3$, $R^4$, $R^5$, $R^6$, and $R^7$ are as described above, and the sulfur is a chiral center, to form the enantiomerically-enriched tetrahydrobenzothiepine-1-oxide.

Preferably, $R^3$ has the formula (VI):

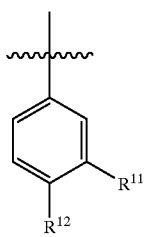

(VI)

wherein and $R^{11}$ and $R^{12}$ are independently selected from the group consisting of alkyl, polyether, fluoride, chloride, bromide, iodide, $NR^{19}R^{20}$, $NR^{20}C(O)R^{19}$, and $OR^{19}$, wherein:

said alkyl and polyether can be further substituted with $SO_3R^{15}$, $N^+R^{15}R^{17}R^{18}A^-$, and quaternary heteroaryl;

$R^{19}$ is selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, polyether, alkylarylalkyl, alkylheteroarylalkyl, alkylheterocyclealkyl, heterocyclealkyl, heteroarylalkyl, quaternary heterocyclealkyl, alkylammoniumalkyl, carboxyalkylaminocarbonylalkyl, and quaternary heteroarylalkyl;

said $R^{19}$ alkyl, alkenyl, alkynyl, arylalkyl, heterocycle, and polyalkyl optionally have one or more carbons replaced by O, $NR^{15}$, $N^+R^{15}R^{16}A^-$, S, SO, $SO_2$, $S^+R^{15}A^-$, $PR^{15}$, $P^+R^{15}R^{16}A^-$, $P(O)R^{15}$, phenylene, carbohydrate, amino acid, peptide, or polypeptide;

$R^{19}$ is optionally substituted with one or more groups selected from the group consisting of hydroxy, amino, sulfo, carboxy, sulfoalkyl, carboxyalkyl, sulfoalkyl, alkyl, heterocycle, heteroaryl, quaternary heterocyclealkyl, quaternary heteroarylalkyl, guanidinyl, quaternary heterocycle, quaternary heteroaryl, $OR^{15}$, $NR^{15}R^{16}$, $N^+R^{15}R^{17}R^{18}A^-$, $SR^{15}$, $S(O)R^{15}$, $SO_2R^{15}$, $SO_3R^{15}$, oxo, $CO_2R^{15}$, CN, halogen, $CONR^{15}R^{16}$, $SO_2OM$, $SO_2NR^{15}R^{16}$, $PO(OR^{22})OR^{23}$, $P^+R^{15}R^{16}R^{17}A^-$, $S^+R^{15}R^{16}A^-$, and C(O)OM, wherein $A^-$ a pharmaceutically acceptable anion, and M is a pharmaceutically acceptable cation, $R^{15}$ and $R^{16}$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboalkylamino, heteroarylalkyl, heterocyclealkyl, and alkylammoniumalkyl;

$R^{17}$ and $R^{18}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^{15}$, $NR^{15}R^{16}$, $SR^{15}$ $S(O)R^{15}$, $SO_2R^{15}$, $SO_3R^{15}$, $CO_3R^{15}$, CN, halogen, oxo, and $CONR^{15}R^{16}$, wherein $R^{15}$ and $R^{16}$ are as defined above, or $R^{17}$ and $R^{18}$ together with the nitrogen or carbon atom to which they are attached form a cyclic ring; and $R^{22}$ and $R^{23}$ are independently selected from the substituents constituting $R^{15}$ and M; and $R^{13}$ and $R_{14}$ are hydrogen.

Preferably, $R^3$ is 4-methoxyphenyl or a group having the structure of formula (IIa) wherein the structure of formula (IIa) is in the 4-position. More preferably, $R^3$ is a group having the structure of formula (IIa).

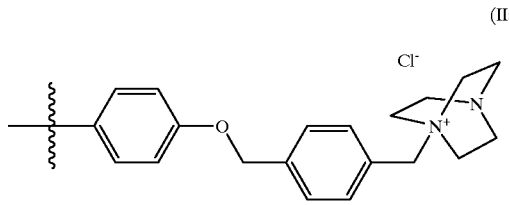

(IIa)

Surprisingly, the cyclization reaction of the enantiomerically-enriched aryl-3-propanalsulfoxide (II) proceeds with a high degree of stereoselectivity at the 4-and 5-positions of the seven-member ring of the tetrahydrobenzothiepine-1-oxide. For example, reaction conditions can be selected to produce predominantly a (4R,5R)-tetrahydrobenzothiepine-1-oxide or to produce predominantly a (4S, 5S)-tetrahydrobenzothiepine-1-oxide.

In one embodiment of the present invention, the cyclization of the enantiomerically-enriched aryl-3-propanalsulfoxide (III) is performed in the presence of a base, for example alkoxide bases. A particularly useful base for this cyclization is potassium t-butoxide.

The enantiomerically-enriched aryl-3-propanalsulfoxide (II) can be obtained, for example, by oxidizing an enantiomerically-enriched aryl-3-hydroxypropylsulfoxide having the formula (III):

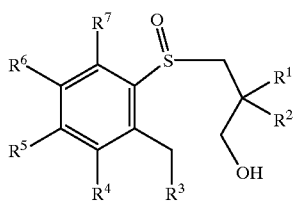

(III)

wherein $R^1$, $R^2$, $R^3$, $R^4$, $R^5$, $R^6$, and $R^7$ are as described above, to form the enantiomerically-enriched aryl-3-propanalsulfoxide.

In one embodiment of the present invention, the oxidation of the enantiomerically-enriched aryl-3-hydroxypropyl-sulfoxide (III) is performed, for example, in the presence of a sulfur trioxide complex such as sulfur trioxide pyridine complex. In another embodiment of the present invention, the oxidation of the enantiomerically-enriched aryl-3-hydroxypropyl-sulfoxide (III) can be performed in the presence of a pyridinium-chromium complex.

In yet another embodiment of the present invention, the enantiomerically-enriched aryl-3-hydroxypropylsulfoxide can be obtained by oxidizing under enantioselective oxidation conditions an aryl-3-hydroxypropylsulfide having the formula (IV):

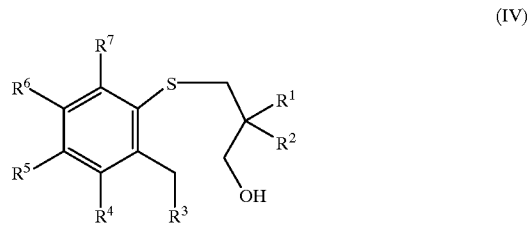

(IV)

wherein $R^1$, $R^2$, $R^3$, $R^4$, $R^5$, $R^6$, and $R^7$ are as described above, to form the enantiomerically-enriched aryl-3-hydroxy-propylsulfoxide.

The enantioselective oxidation conditions can comprise a titanium (IV) alcoholate and a dialkyltartrate. Preferably, the titanium (IV) alcoholate is titanium (IV) isopropoxide and the dialkyltartrate is diethyl-D-tartrate. Optionally, the enantioselective oxidation conditions can further comprise a hydroperoxide compound having the formula (V):

$R^8$—O—O—H (V)

wherein $R^8$ is a moiety selected from among H, alkyl, carboalkyl, benzyl, benzoyl, and cumyl. Preferably, $R^8$ is alkyl or cumyl, more preferably t-butyl or cumyl. Additional examples of hydroperoxide compounds useful for enantioselective oxidations in the present invention can be found in Zhao et al., *Tetrahedron*, 1987, 43(21), 5135–5144.

In another embodiment of the present invention, the enantioselective oxidation conditions for the conversion of the aryl-3-hydroxypropylsulfide (IV) to the aryl-3-hydroxypropylsulfoxide (III) can comprise a chiral (salen) metal complex and an oxidizing agent. The oxidizing agent can be, for example, hydrogen peroxide, a dialkyl peroxide, or an iodosylaryne such as iodobenzene diacetate. Preferably the oxidizing agent is iodobenzene diacetate. The (salen)metal complex is preferably (S,S)-(+)-N,N'-bis(3,5-di-tert-butylsalicyclidene)-1,2-cyclohexanediaminomanganese (III) chloride. Additional examples of (salen)metal complexes useful in the present invention can be found in Palucki et al., *Tetrahedron Letters*, 1992, 33 (47), 7111–7114, and in Saski et al., *Bull. Chem. Soc. Jpn.*, 1991, 64, 1318–1324.

In yet another embodiment of the present invention, the enantioselective oxidation conditions for the conversion of the aryl-3-hydroxypropylsulfide (IV) to the aryl-3-hydroxypropylsulfoxide (III) can comprise a chiral oxaziridine. Preferably, the chiral oxaziridine is (1R)-(−)-(8,8-dichloro-10-camphor-sulfonyl)oxaziridine or (1S)-(+)-(8,8-dichloro-10-camphor-sulfonyl)oxaziridine. More preferably, the chiral oxaziridine is (1R)-(−)-(8,8-dichloro-10-camphor-sulfonyl)oxaziridine. Additional examples of chiral oxaziridines useful in the present invention can be found in Davis et al., *J. Am. Chem. Soc.*, 1992, 114(4), 1428–1437.

The method of the present invention can also be used to prepare an enantiomerically-enriched tetrahydrobenzothiepine-1,1-dioxide having the formula (VII):

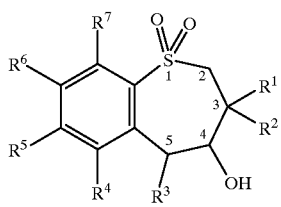

(VII)

wherein $R^1$, $R^2$, $R^3$, $R^4$, $R^5$, $R^6$, and $R^7$ are as described above and wherein the method comprises oxidizing an enantiomerically-enriched tetrahydrobenzothiepine-1-oxide (I) to the enantiomerically-enriched tetrahydrobenzo-thiepine-1,1-dioxide (VII). The oxidation can performed in the presence of a peroxycarboxylic acid, preferably m-chloroperoxybenzoic acid. The enantiomerically-enriched tetrahydrobenzothiepine-1-oxide (I) can be prepared by any of the procedures described above. If desired, the enantiomerically-enriched tetrahydrobenzo-thiepine-1,1-dioxide (VII) can be used in further reaction sequences.

In still another embodiment, the present invention provides an ileal bile acid transport-inhibiting compound (IBAT inhibitors) useful for the prophylaxis or treatment of cardiovascular disease including hypercholesterolemia and atherosclerosis, said IBAT inhibitor compounds being shown in Table 1.

TABLE 1

| Compound Number | Structure and Name | Human TC IC$_{50}$ ($\mu$M) |
| --- | --- | --- |
| (4R, 5R)-XXVII | (4R, 5R)-1-[[4-[[4-[3,3-Dibutyl-7-(dimethylamino)-2,3,4,5-tetrahydro-4-hydroxy-1,1-dioxido-1-benzothienpin-5-yl]-phenoxy]methyl]phenyl]methyl]-4-aza-1-azoniabicyclo-[2.2.2] octane chloride | 0.00028 |
| (4S, 5S)-XXVII | (4S, 5S)-1-[[4-[[4-[3,3-Dibutyl-7-(dimethylamino)-2,3,4,5-tetrahydro-4-hydroxy-1,1-dioxido-1-benzothienpin-5-yl]-phenoxy]methyl]phenyl]methyl]-4-aza-1-azoniabicyclo-[2.2.2]octane chloride | 0.051 |

Biological Assays

The utility of the compounds of the present invention is shown by the following assays. These assays are performed in vitro using a procedure recognized to show the utility of the present invention.

In Vitro Assay of compounds that inhibit IBAT-mediated uptake of [$^{14}$C]-Taurocholate (TC) in H14 Cells Baby hamster kidney cells (BHK) transfected with the cDNA of human IBAT (H14 cells) are seeded at 60,000 cells/well in 96 well Top-Count tissue culture plates for assays run within in 24 hours of seeding, 30,000 cells/well for assays run within 48 hours, and 10,000 cells/well for assays run within 72 hours.

On the day of assay, the cell monolayer is gently washed once with 100 µl assay buffer (Dulbecco's Modified Eagle's medium with 4.5 g/L glucose+0.2% (w/v) fatty acid free bovine serum albumin-(FAF)BSA). To each well 50 µl of a two-fold concentrate of test compound in assay buffer is added along with 50 µl of 6 µM [$^{14}$C]-taurocholate in assay buffer (final concentration of 3 µM [$^{14}$C]-taurocholate). The cell culture plates are incubated 2 hours at 37° C. prior to gently washing each well twice with 100 µl 4° C. Dulbecco's phosphate-buffered saline (PBS) containing 0.2% (w/v) (FAF)BSA. The wells are then gently washed once with 100 µl 4° C. PBS without (FAF)BSA. To each 200 µl of liquid scintillation counting fluid is added, the plates are heat sealed and shaken for 30 minutes at room temperature prior to measuring the amount of radioactivity in each well on a Packard Top-Count instrument.

In Vitro Assay of compounds that inhibit uptake of [$^{14}$C]-Alanine

The alanine uptake assay is performed in an identical fashion to the taurocholate assay, with the exception that labeled alanine is substituted for the labeled taurocholate.

Detailed Preparative Methods

The starting materials for use in the methods of preparation of the invention are known or can be prepared by conventional methods known to a skilled person or in an analogous manner to processes described in the art.

Generally, the preparative methods of the present invention can be performed as follows.

As shown in Figure I, reaction of phenol (VIII) with sodium hydride (or another base which will extract a hydrogen from the benzene ring of phenol (VIII)) followed by addition of chloromethyl compound (IX) yields 2-hydroxybenzyl compound (X). Treatment of 2-hydroxybenzyl compound (X) with sodium hydride (or another base which will extract a hydrogen from compound (X)) and then with dimethylthiocarbamoyl chloride produces thiocarbamate (XI). Thiocarbamate (XI) is refluxed in a solvent such as diphenyl ether for a period of time adequate to effect the rearrangement of thiocarbamate (XI) (e.g., overnight), isolated by filtration, and then treated with a base such as sodium hydroxide, optionally in a solvent such as methanolic tetrahydrofuran, to produce thiophenol (XII). Treatment of 2,2-disubstituted-1,3-propanediol (XIII, Figure II) with an amine such as triethylamine followed by addition of thionyl chloride produces cyclic sulfite (XIV). The formation of cyclic sulfite (XIV) can optionally be performed in a solvent such as anhydrous methylene chloride. Reaction of cyclic sulfite (XIV) under oxidizing conditions yields cyclic sulfate (XV). For example, the oxidizing conditions can comprise reacting cyclic sulfite (XIV) in the presence of ruthenium (III) chloride and sodium periodate overnight to yield cyclic sulfate (XV). Treatment of thiophenol (XII) with a base capable of removing a hydrogen from the sulfhydryl group of thiophenol (XII) (e.g., sodium hydride) followed by addition of cyclic sulfate (XV) produces aryl-3-hydroxypropylsulfide (IV). Oxidation of aryl-3-hydroxypropylsulfide (IV) with an asymmetric oxidizing agent, for example (1R)-(-)-(8,9-dichloro-10-camphorsulfonyl)oxaziridine, yields aryl-3-hydroxypropylsulfoxide (III). Reaction of aryl-3-hydroxypropylsulfoxide (III) under oxidizing conditions (e.g., in the presence of sulfur trioxide pyridine complex) yields aryl-3-propanalsulfoxide (II). Cyclization of aryl-3-propanalsulfoxide (II) with a base (for example an alkoxide base such as potassium t-butoxide) produces tetrahydrobenzothiepine-1-oxide (I). Oxidation of tetrahydrobenzothiepine-1-oxide (I) with an oxidizing agent, for example m-chloroperoxybenzoic acid, yields tetrahydrobenzothiepine-1,1-dioxide (VII).

Abbreviations used in the foregoing description and in the examples have the following meanings:

| | |
|---|---|
| NaH | sodium hydride |
| ClC(S)NMe$_2$ | dimethylthiocarbamoyl chloride |
| Ph$_2$O | diphenyl ether |
| SO$_3$Py | sulfur trioxide pyridine complex |
| t-BuOK | potassium t-butoxide |
| m-CPBA | m-chloroperoxybenzoic acid |
| THF | tetrahydrofuran |
| LAH | lithium aluminum hydride |
| RT | room temperature |

In reaction FIGS. I and II, $R^1$ and $R^2$ can be independently selected from among substituted and unsubstituted $C_1$ to about $C_{20}$ alkyl, $C_2$ to about $C_{20}$ alkenyl, aryl and heteroaryl. $R^3$ can be selected from among substituted and unsubstituted aryl and heteroaryl. $R^4$, $R^5$, $R^6$, and $R^7$ can be independently selected from among substituted and unsubstituted $C_1$ to about $C_{20}$ alkyl, $C_2$ to about $C_{20}$ alkenyl, aryl, heteroaryl, alkoxy, aryloxy, and from among hydrogen, —NO$_2$, and —NR$^9$N$^{10}$. $R^9$ and $R^{10}$ can be independently selected from among substituted and unsubstituted alkyl, alkenyl, alkynyl, cycloalkyl, aryl, heteroaryl, and from among hydrogen, butoxycarbonyl, carbobenzyloxy, and other amine protecting groups known in the art. Substituent(s) on the various groups can be selected from among alkyl, alkenyl, alkynyl, cycloalkyl, aryl, heteroaryl, alkoxy, aryloxy, —NO$_2$, and halo.

Examples of some specific compounds and reaction conditions which can be used in the method of this invention are provided herein. The following non-limiting examples serve to illustrate various aspects of the present invention.

EXAMPLE 1

Preparation of 4-fluoro-2-((4-methoxyphenyl)methyl)-phenol (XVI)

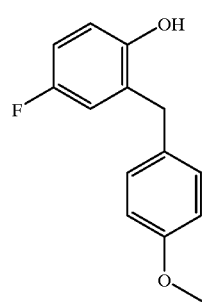

(XVI)

To a stirred solution of 23.66 g of 95% sodium hydride (0.94 mol) in 600 mL of dry toluene was added 100.0 g of 4-fluorophenol (0.89 mol) at 0° C. The mixture was stirred at 90° C. for 1 hour until gas evolution stopped. The mixture was cooled down to room temperature and a solution of 139.71 g of 3-methoxybenzyl chloride (0.89 mol) in 400 mL of dry toluene was added. After refluxing for 24 hours, the mixture was cooled to room temperature and quenched with 500 mL of water. The organic layer was separated, dried over MgSO$_4$, and concentrated under high vacuum. The remaining starting materials were removed by distillation. The crude dark red oil was filtered through a layer of 1 L of silica gel with neat hexane to yield 53.00 g (25.6%) of the product as a pink solid: $^1$H NMR (CDCl$_3$) d 3.79 (s, 3H), 3.90 (s, 2H), 4.58 (s, 1H), 6.70–6.74 (m, 1H), 6.79–6.88 (m, 4H), 7.11–7.16 (m, 2H)

EXAMPLE 2

Preparation of 4-fluoro-2-((4-methoxyphenyl)methyl)-thiophenol (XVII)

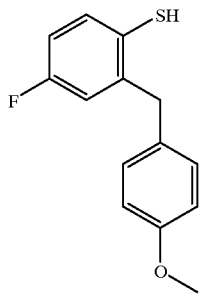

(XVII)

Step 2a. Preparation of thiocarbamate (XVIII).

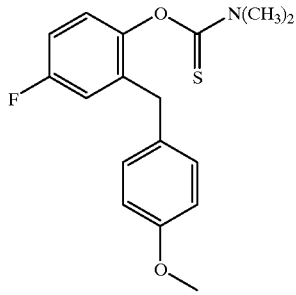

(XVIII)

To a stirred solution of 50.00 g (215.30 mmol) of 4-fluoro-2-((4-methoxyphenyl)methyl)-phenol (XVI) in 500 mL of dry DMF was added 11.20 g of 60% sodium hydride dispersion in mineral oil (279.90 mmol) at 2° C. The mixture was allowed to warm to room temperature and 26.61 g of dimethylthiocarbamoyl chloride (215.30 mmol) was added. The reaction mixture was stirred at room temperature overnight. The mixture was quenched with 100 mL of water in an ice bath. The solution was extracted with 500 mL of diethyl ether. The ether solution was washed with 500 mL of water and 500 mL of brine. The ether solution was dried over MgSO$_4$ and stripped to dryness. The crude product was filtered through a plug of 500 mL silica gel using 5% ethyl acetate/hexane to yield 48.00 g (69.8%) of the product as a pale white solid: $^1$H NMR (CDCl$_3$) d 3.21 (s, 3H), 3.46 (s, 3H), 3.80 (s, 3H), 3.82 (s, 2H), 6.78–6.86 (m, 3H), 6.90–7.00 (m, 2H), 7.09 (d, J=8.7 Hz, 2H)

Step 2b. Rearrangement and hydrolysis of thiocarbamate (XVIII) to 4-fluoro-2-((4-methoxyphenyl)methyl)-thiophenol (XVII).

A stirred solution of 48.00 g (150.29 mmol) of thiocarbamate (XVIII) in 200 mL of diphenyl ether was refluxed at 270° C. overnight. The solution was cooled down to room temperature and filtered through 1 L of silica gel with 2 L of hexane to remove phenyl ether. The rearrangement product was washed with 5% ethyl acetate/hexane to give 46.00 g (95.8%) of the product as a pale yellow solid: $^1$H NMR (CDCl$_3$) d 3.02 (s, 3H), 3.10 (s, 3H), 3.80 (s, 3H), 4.07 (s, 2H), 6.82–6.86 (m, 3H), 6.93 (dt, J=8.4 Hz, 2.7 Hz, 1H), 7.08 (d, J=8.7 Hz, 2H), 7.49 (dd, J=6.0 Hz, 8.7 Hz, 1H).

To a solution of 46.00 g (144.02 mmol) of the rearrangement product (above) in 200 mL of methanol and 200 mL of THF was added 17.28 g of NaOH (432.06 mmol). The mixture was refluxed under nitrogen overnight. The solvents were evaporated off and 200 mL of water was added. The aqueous solution was washed with 200 mL of diethyl ether twice and placed in an ice bath. The aqueous mixture was acidified to pH 6 with concentrated HCl solution. The solution was extracted with 300 mL of diethyl ether twice. The ether layers were combined, dried over MgSO$_4$ and stripped to dryness to afford 27.00 g (75.5%) of the product as a brown oil: $^1$H NMR (CDCl$_3$) d 3.24 (s, 1H), 3.80 (s, 3H), 3.99 (s, 2H), 6.81–6.87 (m, 4H), 7.09 (d, J=8.7 Hz, 2H), 7.27–7.33 (m, 1H).

EXAMPLE 3

Preparation of dibutyl cyclic sulfate (XIX)

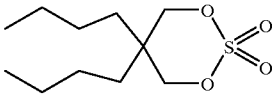

(XIX)

Step 3a. Preparation of 2,2-dibutyl-1,3-propanediol.

To a stirred solution of di-butyl-diethylmalonate (Aldrich) (150g, 0.55 mol in dry THF (700 ml) in an acetone/dry ice bath was added LAH (1 M THF) 662 ml (1.2 eq., 0.66 mol) dropwise maintaining the temperature between −20° C. to 0° C. The reaction was stirred at RT overnight. The reaction was cooled to −20° C. and 40 ml of water, and 80 mL of 10% NaOH and 80 ml of water were added dropwise. The resulting suspension was filtered. The filtrate was dried over sodium sulphate and concentrated in vacuo to give diol 98.4 g (yield 95%) as an oil. MS spectra and proton and carbon NMR spectra were consistent with the product.

Step 3a. Preparation of dibutyl cyclic sulfite (XX).

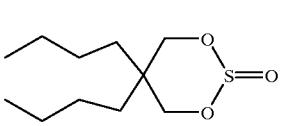

(XX)

A solution of 2,2-dibutyl-1,3-propanediol (103 g, 0.548 mol) and triethylamine (221 g, 2.19 mol) in anhydrous methylene chloride (500 ml) was stirred at 0C under nitrogen. To the mixture, thionyl chloride (97.8 g, 0.82 mol) was added dropwise and within S min the solution turned yellow and then black when the addition was completed within half an hour. The reaction mixture was stirred for 3 hrs. at 0° C. GC showed that there was no starting material left. The mixture was washed with ice water twice then with brine twice. The organic phase was dried over magnesium sulfate and concentrated under vacuum to give 128 g (100%) of the dibutyl cyclic sulfite (XX) as a black oil. Mass spectrum (MS) was consistent with the product.

Step 3b. Oxidation of dibutyl cyclic sulfite (XX) to dibutyl cyclic sulfate (XIX).

To a solution of the dibutyl cyclic sulfite (XX) (127.5 g, 0.54 mol) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. GC showed that there was no starting material left. The mixture was extracted with 300 ml of ether and the ether extract was washed three times with brine. The organic phase was dried over magnesium sulfate and passed through celite. The filtrate was concentrated under vacuum and to give 133 g (97.8%) of the dibutyl cyclic sulfate (XIX) as an oil. Proton and carbon NMR and MS were consistent with the product.

EXAMPLE 4

Preparation of aryl-3-hydroxypropylsulfide (XXI)

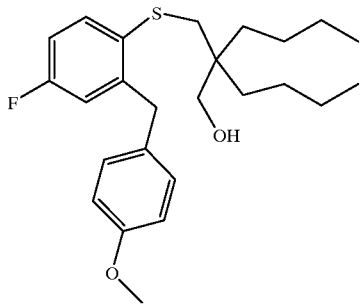

(XXI)

To a stirred solution of 27.00 g (108.73 mmol) of 4-fluoro-2-((4-methoxyphenyl)methyl)thiophenol (XVII) in 270 mL of diglyme was added 4.35 g of 60% sodium hydride dispersion in mineral oil (108.73 mmol) at 0° C. After gas evolution ceased, 29.94 g (119.60 mmol) of the dibutyl cyclic sulfate (XIX) was added at 0° C. and stirred for 10 minutes. The mixture was allowed to warm up to room temperature and stirred overnight. The solvent was evaporated and 200 mL of water was added. The solution was washed with 200 mL of diethyl ether and added 25 mL of concentrated sulfuric acid to make a 2.0 M solution that was refluxed overnight. The solution was extracted with ethyl acetate and the organic solution was dried over $MgSO_4$ and concentrated in vacuo. The crude aryl-3-hydroxypropylsulfide (XXI) was purified by silica gel chromatography (Waters Prep 500) using 8% ethyl acetate/hexane to yield 33.00 g (72.5%) of the product as a light brown oil: $^1H$ NMR ($CDCl_3$) d 0.90 (t, J=7.1 Hz, 6H), 1.14–1.34 (m, 12H), 2.82 (s, 2H), 3.48 (s, 2H), 3.79 (s, 3H), 4.10 (s, 2H), 6.77–6.92 (m, 4H), 7.09 (d, J=8.7 Hz, 2H), 7.41 (dd, J=8.7 Hz, 5.7 Hz, 1H).

EXAMPLE 5

Preparation of enantiomerically-enriched aryl-3-hydroxypropylsulfoxide (XXII)

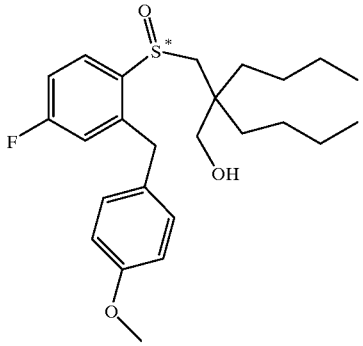

(XXII)

\* = chiral center

To a stirred solution of 20.00 g (47.78 mmol) of aryl-3-hydroxypropylsulfide (XXI) in 1 L of methylene chloride was added 31.50 g of 96% (1R)-(−)-(8,8-dichloro-10-camphor-sulfonyl)oxaziridine (100.34 mmol, Aldrich) at 2° C. After all the oxaziridine dissolved the mixture was placed into a −30° C. freezer for 72 hours. The solvent was evaporated and the crude solid was washed with 1 L of hexane. The white solid was filtered off and the hexane solution was concentrated in vacuo. The crude oil was purified on a silica gel column (Waters Prep 500) using 15% ethyl acetate/hexane to afford 19.00 g (95%) of the enantiomerically-enriched aryl-3-hydroxypropylsulfoxide (XXII) as a colorless oil: $^1H$ NMR ($CDCl_3$) d 0.82–0.98 (m, 6H), 1.16–1.32 (m, 12H), 2.29 (d, J=13.8 Hz, 1H), 2.77 (d, J=13.5 Hz, 1H), 3.45 (d, J=12.3 Hz, 1H), 3.69 (d, J=12.3 Hz, 1H), 3.79 (s, 3H), 4.02 (q, J=15.6 Hz, 1H), 6.83–6.93 (m, 3H), 7.00 (d, J=8.1 Hz, 2H), 7.18–7.23 (m, 1H), 7.99–8.04 (m, 1H). Enantiomeric excess was determined by chiral HPLC on a (R,R)-Whelk-O column using 5% ethanol/hexane as the eluent. It showed to be 78% e.e. with the first eluting peak as the major product.

EXAMPLE 6

Preparation of enantiomerically-enriched aryl-3-propanalsulfoxide (XXIII)

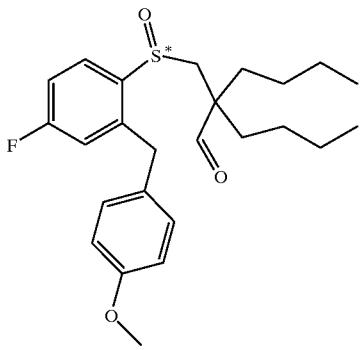

(XXIII)

\* = chiral center

To a stirred solution of 13.27 g of triethylamine (131.16 mmol, Aldrich) in 200 mL dimethyl sulfoxide were added 19.00 g (43.72 mmol) of enantiomerically-enriched aryl-3-hydroxypropylsulfoxide (XXII) and 20.96 g of sulfur trioxide-pyridine (131.16 mmol, Aldrich) at room temperature. After the mixture was stirred at room temperature for 48 hours, 500 mL of water was added to the mixture and stirred vigorously. The mixture was then extracted with 500 mL of ethyl acetate twice. The ethyl acetate layer was separated, dried over MgSO$_4$, and concentrated in vacuo. The crude oil was filtered through 500 mL of silica gel using 15% ethyl acetate/hexane to give 17.30 g (91%) of the enantiomerically-enriched aryl-3-propanalsulfoxide (XXIII) as a light orange oil: $^1$H NMR (CDCl$_3$) d 0.85–0.95 (m, 6H), 1.11–1.17 (m, 4H), 1.21–1.39 (m, 4H), 1.59–1.76 (m, 4H), 1.89–1.99 (m, 1H), 2.57 (d, J=14.1 Hz, 1H), 2.91 (d, J=13.8 Hz, 1H), 3.79 (s, 3H), 3.97 (d, J=15.9 Hz, 1H), 4,12 (d, J=15.9 Hz, 1H), 6.84–6.89 (m, 3H), 7.03 (d, J=8.4 Hz, 2H), 7.19 (dt, J=8.4 Hz, 2.4 Hz, 1H), 8.02 (dd, J=8.7 Hz, 5.7 Hz, 1H), 9.49 (s, 1H).

EXAMPLE 7

Preparation of the enantiomerically-enriched tetrahydrobenzothiepine-1-oxide ((4R,5R)-XXIV)

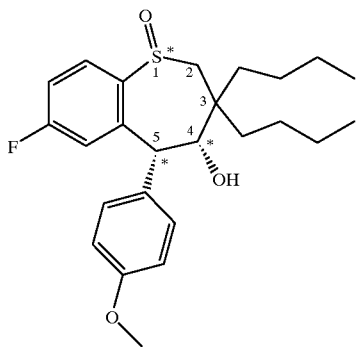

((4R, 5R) - XXIV)

* = chiral center

To a stirred solution of 17.30 g (39.99 mmol) of enantiomerically-enriched aryl-3-propanalsulfoxide (XXIII) in 300 mL of dry THF at −15° C. was added 48 mL of 1.0 M potassium t-butoxide in THF (1.2 equivalents) under nitrogen. The solution was stirred at −15° C. for 4 hours. The solution was then quenched with 100 mL of water and neutralized with 4 mL of concentrated HCl solution at 0° C. The THF layer was separated, dried over MgSO$_4$, and concentrated in vacuo. The enantiomerically-enriched tetrahydrobenzothiepine-1-oxide ((4R,5R)-XXIV) was purified by silica gel chromatography (Waters Prep 500) using 15% ethyl acetate/hexane to give 13.44 g (77.7%) of the product as a white solid: $^1$H NMR (CDCl$_3$) d 0.87–0.97 (m, 6H), 1.16–1.32 (m, 4H), 1.34–1.48 (m, 4H), 1.50–1.69 (m, 4H), 1.86–1.96 (m, 1H), 2.88 (d, J=13.0 Hz, 1H), 3.00 (d, J=13.0 Hz, 1H), 3.85 (s, 3H), 4.00 (s, 1H), 4.48 (s, 1H), 6.52 (dd, J=9.9 Hz, 2.4 Hz, 1H), 6.94 (d, J=9 Hz, 2H), 7.13 (dt, J=8.4 Hz, 2.4 Hz, 1H), 7.38 (d, J=8.7 Hz, 2H), 7.82 (dd, J=8.7 Hz, 5.7 Hz, 1H)

EXAMPLE 8

Preparation of enantiomerically-enriched tetrahydrobenzothiepine-1,1-dioxide ((4R,5R)-XXV)

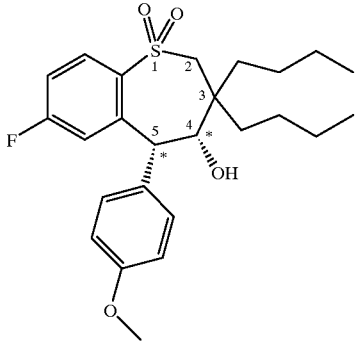

((4R, 5R) - XXV)

* = chiral center

To a stirred solution of 13.44 g (31.07 mmol) of enantiomerically-enriched tetrahydrobenzothiepine-1-oxide ((4R,5R)-XXIV) in 150 mL of methylene chloride was added 9.46 g of 68% m-chloroperoxybenzoic acid (37.28 mmol, Sigma) at 0° C. After stirring at 0° C. for 2 hours, the mixture was allowed to warm up to room temperature and stirred for 4 hours. 50 mL of saturated Na$_2$SO$_3$ was added into the mixture and stirred for 30 minutes. The solution was then neutralized with 50 mL of saturated NaHCO$_3$ solution. The methylene chloride layer was separated, dried over MgSO$_4$, and concentrated in vacuo to give 13.00 g (97.5%) of the enantiomerically-enriched tetrahydrobenzothiepine-1,1-dioxide ((4R,5R)-XXV) as a light yellow solid: $^1$H NMR (CDCl$_3$) d 0.89–0.95 (m, 6H), 1.09–1.42 (m, 12H), 2.16–2.26 (m, 1H), 3.14 (q, J=15.6 Hz, 1H), 3.87 (s, 3H), 4.18 (s, 1H), 5.48 (s, 1H), 6.54 (dd, J=10.2 Hz, 2.4 Hz, 1H), 6.96–7.07 (m, 3H), 7.40 (d, J=8.1 Hz, 2H), 8.11 (dd, J=8.6 Hz, 5.9 Hz, 1H).

EXAMPLE 9

Preparation of enantiomerically-enriched 7-(dimethylamino)tetrahydrobenzothiepine-1,1-dioxide ((4R,5R)-XXVI)

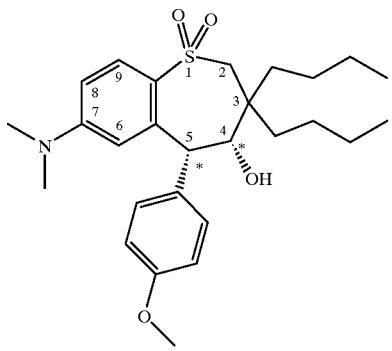

((4R, 5R) - XXVI)

* = chiral center

To a solution of 13.00 g (28.98 mmol) of enantiomerically-enriched tetrahydrobenzothiepine-1,1- dioxide ((4R,5R)-XXV) in 73 mL of dimethylamine (2.0 M in THF, 146 mmol) in a Parr Reactor was added ca. 20 mL of neat dimethylamine. The mixture was sealed and stirred at 110° C. overnight, and cooled to ambient temperature. The excess dimethylamine was evaporated. The crude oil was dissolved in 200 mL of ethyl acetate and washed with 100 mL of water, dried over MgSO$_4$ and concentrated in vacuo. Purification on a silica gel column (Waters Prep 500) using 20% ethyl acetate/hexane gave 12.43 g (90.5%) of the enantiomerically-enriched 7-(dimethylamino) tetrahydrobenzothiepine-1,1-dioxide ((4R,5R)-XXVI) as a colorless solid: $^1$H NMR (CDCl$_3$) d 0.87–0.93 (m, 6H), 1.10–1.68 (m, 12H), 2.17–2.25 (m, 1H), 2.81 (s, 6H), 2.99 (d, J=15.3 Hz, 1H), 3.15 (d, J=15.3 Hz, 1H), 3.84 (s, 3H), 4.11 (d, J=7.5 Hz, 1H), 5.49 (s, 1H), 5.99 (d, J=2.4 Hz, 1H), 6.51 (dd, J=8.7 Hz, 2.4 Hz, 1H), 6.94 (d, J=8.7 Hz, 2H), 7.42 (d, J=8.4 Hz, 2H), 7.90 (d, J=8.7 Hz, 1H). The product was determined to have 78% e.e. by chiral HPLC on a Chiralpak AD column using 5% ethanol/hexane as the eluent. Recrystallization of this solid from ethyl acetate/hexane gave 1.70 g of the racemic product. The remaining solution was concentrated and recrystallized to give 9.8 g of colorless solid. Enantiomeric excess of this solid was determined by chiral HPLC on a Chiralpak AD column using 5% ethanol/hexane as the eluent. It showed to have 96% e.e with the first eluting peak as the major product.

EXAMPLE 10

Preparation of enantiomerically-enriched (4R,5R)-1-[[4-[[4-[3,3-Dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane chloride ((4R,5R)-XXVII)

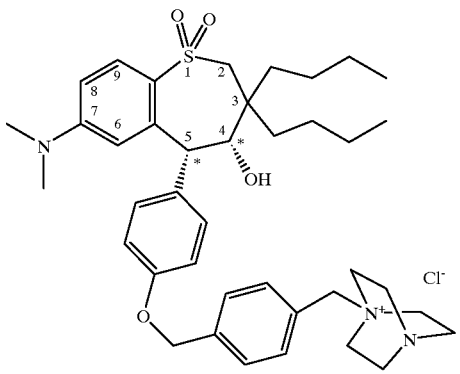

((4R, 5R) - XXVII)

* = chiral center

Step 1. Preparation of 4-fluoro-2-((4-methoxyphenyl) methyl)-phenol

To a stirred solution of 23.66 g of 95% sodium hydride (0.94 mol) in 600 mL of dry toluene was added 100.0 g of 4-fluorophenol (0.89 mol) at 0° C. The mixture was stirred at 90° C. for 1 hour until gas evolution stopped. The mixture was cooled down to room temperature and a solution of 139.71 g of 3-methoxybenzyl chloride (0.89 mol) in 400 mL of dry toluene was added. After refluxing for 24 hours, the mixture was cooled to room temperature and quenched with 500 mL of water. The organic layer was separated, dried over MgSO$_4$, and concentrated under high vacuum. The remaining starting materials were removed by distillation. The crude dark red oil was filtered through a layer of 1 L of silica gel with neat hexane to yield 53.00 g (25.6%) of the product as a pink solid: $^1$H NMR (CDCl$_3$) d 3.79 (s, 3H), 3.90 (s, 2H), 4.58 (s, 1H), 6.70–6.74 (m, 1H), 6.79–6.88 (m, 4H), 7.11–7.16 (m, 2H).

Step 2. Preparation of 4-fluoro-2-((4-methoxyphenyl) methyl)-thiophenol Step 2a. Preparation of thiocarbamate To a stirred solution of 50.00 g (215.30 mmol) of 4-fluoro-2-((4-methoxyphenyl)methyl)-phenol in 500 mL of dry DMF was added 11.20 g of 60% sodium hydride dispersion in mineral oil (279.90 mmol) at 2° C. The mixture was allowed to warm to room temperature and 26.61 g of dimethylthiocarbamoyl chloride (215.30 mmol) was added. The reaction mixture was stirred at room temperature overnight. The mixture was quenched with 100 mL of water in an ice bath. The solution was extracted with 500 mL of diethyl ether. The ether solution was washed with 500 mL of water and 500 mL of brine. The ether solution was dried over MgSO$_4$ and stripped to dryness. The crude product was filtered through a plug of 500 mL silica gel using 5% ethyl acetate/hexane to yield 48.00 g (69.8%) of the product as a pale white solid: $^1$H NMR (CDCl$_3$) d 3.21 (s, 3H), 3.46 (s, 3H), 3.80 (s, 3H), 3.82 (s, 2H), 6.78–6.86 (m, 3H), 6.90–7.00 (m, 2H), 7.09 (d, J=8.7 Hz, 2H).

Step 2b. Rearrangement and hydrolysis of thiocarbamate to 4-fluoro-2-((4-methoxyphenyl)methyl)-thiophenol A stirred solution of 48.00 g (150.29 mmol) of thiocarbamate (obtained from Step 2a) in 200 mL of diphenyl ether was refluxed at 27° C. overnight. The solution was cooled down to room temperature and filtered through 1 L of silica gel with 2 L of hexane to remove phenyl ether. The rearrangement product was washed with 5% ethyl acetate/hexane to give 46.00 g (95.8%) of the product as a pale yellow solid: $^1$H NMR (CDCl$_3$) d 3.02 (s, 3H), 3.10 (s, 3H), 3.80 (s, 3H), 4.07 (s, 2H), 6.82–6.86 (m, 3H), 6.93 (dt, J=8.4 Hz, 2.7 Hz, 1H), 7.08 (d, J=8.7 Hz, 2H), 7.49 (dd, J=6.0 Hz, 8.7 Hz, 1H).

To a solution of 46.00 g (144.02 mmol) of the rearrangement product (above) in 200 mL of methanol and 200 mL of THF was added 17.28 g of NaOH (432.06 mmol). The mixture was refluxed under nitrogen overnight. The solvents were evaporated off and 200 mL of water was added. The aqueous solution was washed with 200 mL of diethyl ether twice and placed in an ice bath. The aqueous mixture was acidified to pH 6 with concentrated HCl solution. The solution was extracted with 300 mL of diethyl ether twice. The ether layers were combined, dried over MgSO$_4$ and stripped to dryness to afford 27.00 g (75.5%) of the product as a brown oil: $^1$H NMR (CDCl$_3$) d 3.24 (s, 1H), 3.80 (s, 3H), 3.99 (s, 2H), 6.81–6.87 (m, 4H), 7.09 (d, J=8.7 Hz, 2H), 7.27–7.33 (m, 1H).

Step 3. Preparation of dibutyl cyclic sulfate Step 3a. Preparation of 2,2-dibutyl-1,3-propanediol.

To a stirred solution of di-butyl-diethylmalonate (Aldrich) (150 g, 0.55 mol in dry THF (700 ml) in an acetone/dry ice bath was added LAH (1 M THF) 662 ml (1.2 eq., 0.66 mol) dropwise maintaining the temperature between –20 to 0° C. The reaction was stirred at RT overnight. The reaction was cooled to –20° C. and 40 ml of water, and 80 mL of 10% NaOH and 80 ml of water were added dropwise. The resulting suspension was filtered. The filtrate was dried over sodium sulphate and concentrated in vacuo to give diol 98.4 g (yield 95%) as an oil. MS spectra and proton and carbon NMR spectra were consistent with the product.

Step 3b. Preparation of dibutyl cyclic sulfite

A solution of 2,2-dibutyl-1,3-propanediol (103 g, 0.548 mol, obtained from Step 3a) and triethylamine (221 g, 2.19 mol) in anhydrous methylene chloride (500 ml) was stirred at 0° C. under nitrogen. To the mixture, thionyl chloride (97.8 g, 0.82 mol) was added dropwise and within 5 min the solution turned yellow and then black when the addition was completed within half an hour. The reaction mixture was stirred for 3 hrs. at 0° C. GC showed that there was no starting material left. The mixture was washed with ice water twice then with brine twice. The organic phase was dried over magnesium sulfate and concentrated under vacuum to give 128 g (100%) of the dibutyl cyclic sulfite as a black oil. Mass spectrum (MS) was consistent with the product.

Step 3b. Oxidation of dibutyl cyclic sulfite to dibutyl cyclic sulfate

To a solution of the dibutyl cyclic sulfite (XX) (127.5 g, 0.54 mol, obtained from Step 3b) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. GC showed that there was no starting material left. The mixture was extracted with 300 ml of ether and the ether extract was washed three times with brine. The organic phase was dried over magnesium sulfate and passed through celite. The filtrate was concentrated under vacuum and to give 133 g (97.8%) of the dibutyl cyclic sulfate as an oil. Proton and carbon NMR and MS were consistent with the product.

Step 4. Preparation of aryl-3-hydroxypropylsulfide

To a stirred solution of 27.00 g (108.73 mmol) of 4-fluoro-2-((4-methoxyphenyl)methyl)thiophenol (obtained from Step 2) in 270 mL of diglyme was added 4.35 g of 60% sodium hydride dispersion in mineral oil (108.73 mmol) at 0° C. After gas evolution ceased, 29.94 g (119.60 mmol) of the dibutyl cyclic sulfate (obtained from Step 3c) was added at 0° C. and stirred for 10 minutes. The mixture was allowed to warm up to room temperature and stirred overnight. The solvent was evaporated and 200 mL of water was added. The solution was washed with 200 mL of diethyl ether and added 25 mL of concentrated sulfuric acid to make a 2.0 M solution that was refluxed overnight. The solution was extracted with ethyl acetate and the organic solution was dried over $MgSO_4$ and concentrated in vacuo. The crude aryl-3-hydroxypropylsulfide was purified by silica gel chromatography (Waters Prep 500) using 8% ethyl acetate/hexane to yield 33.00 g (72.5%) of the product as a light brown oil: $^1$H NMR ($CDCl_3$) d 0.90 (t, J=7.1 Hz, 6H), 1.14–1.34 (m, 12H), 2.82 (s, 2H), 3.48 (s, 2H), 3.79 (s, 3H), 4.10 (s, 2H), 6.77–6.92 (m, 4H), 7.09 (d, J=8.7 Hz, 2H), 7.41 (dd, J=8.7 Hz, 5.7 Hz, 1H)

Step 5. Preparation of enantiomerically-enriched aryl-3-hydroxypropylsulfoxide

To a stirred solution of 20.00 g (47.78 mmol) of aryl-3-hydroxypropylsulfide (obtained from Step 4) in 1 L of methylene chloride was added 31.50 g of 96% (1R)-(–)-(8, 8-dichloro-10-camphor-sulfonyl)oxaziridine (100.34 mmol, Aldrich) at 2° C. After all the oxaziridine dissolved the mixture was placed into a –30° C. freezer for 72 hours. The solvent was evaporated and the crude solid was washed with 1 L of hexane. The white solid was filtered off and the hexane solution was concentrated in vacuo. The crude oil was purified on a silica gel column (Waters Prep 500) using 15% ethyl acetate/hexane to afford 19.00 g (95%) of the enantiomerically-enriched aryl-3-hydroxypropylsulfoxide as a colorless oil: $^1$H NMR ($CDCl_3$) d 0.82–0.98 (m, 6H), 1.16–1.32 (m, 12H), 2.29 (d, J=13.8 Hz, 1H), 2.77 (d, J=13.5 Hz, 1H), 3.45 (d, J=12.3 Hz, 1H), 3.69 (d, J=12.3 Hz, 1H), 3.79 (s, 3H), 4.02 (q, J=15.6 Hz, 1H), 6.83–6.93 (m, 3H), 7.00 (d, J=8.1 Hz, 2H), 7.18–7.23 (m, 1H), 7.99–8.04 (m, 1H). Enantiomeric excess was determined by chiral HPLC on a (R,R)-Whelk-O column using 5% ethanol/hexane as the eluent. It showed to be 78% e.e. with the first eluting peak as the major product.

Step 6. Preparation of enantiomerically-enriched aryl-3-propanalsulfoxide

To a stirred solution of 13.27 g of triethylamine (131.16 mmol, Aldrich) in 200 mL dimethyl sulfoxide were added 19.00 g (43.72 mmol) of enantiomerically-enriched aryl-3-hydroxypropylsulfoxide (obtained from Step 5) and 20.96 g of sulfur trioxide-pyridine (131.16 mmol, Aldrich) at room temperature. After the mixture was stirred at room temperature for 48 hours, 500 mL of water was added to the mixture and stirred vigorously. The mixture was then extracted with 500 mL of ethyl acetate twice. The ethyl acetate layer was separated, dried over $MgSO_4$, and concentrated in vacuo. The crude oil was filtered through 500 mL of silica gel using 15% ethyl acetate/hexane to give 17.30 g (91%) of the enantiomerically-enriched aryl-3-propanalsulfoxide as a light orange oil: $^1$H NMR ($CDCl_3$) d 0.85–0.95 (m, 6H), 1.11–1.17 (m, 4H), 1.21–1.39 (m, 4H), 1.59–1.76 (m, 4H), 1.89–1.99 (m, 1H), 2.57 (d, J=14.1 Hz, 1H), 2.91 (d, J=13.8 Hz, 1H), 3.79 (s, 3H), 3.97 (d, J=15.9 Hz, 1H), 4,12 (d, J=15.9 Hz, 1H), 6.84–6.89 (m, 3H), 7.03 (d, J=8.4 Hz, 2H), 7.19 (dt, J=8.4 Hz, 2.4 Hz, 1H), 8.02 (dd, J=8.7 Hz, 5.7 Hz, 1H), 9.49 (s, 1H).

Step 7. Preparation of the enantiomerically-enriched tetrahydrobenzothiepine-1-oxide (4R,5R)

To a stirred solution of 17.30 g (39.99 mmol) of enantiomerically-enriched aryl-3-propanalsulfoxide (obtained from Step 6) in 300 mL of dry THF at –15° C. was added 48 mL of 1.0 M potassium t-butoxide in THF (1.2 equivalents) under nitrogen. The solution was stirred at –15° C. for 4 hours. The solution was then quenched with 100 mL of water and neutralized with 4 mL of concentrated HCl solution at 0° C. The THF layer was separated, dried over $MgSO_4$, and concentrated in vacuo. The enantiomerically-enriched tetrahydrobenzothiepine-1-oxide (4R,5R) was purified by silica gel chromatography (Waters Prep 500) using 15% ethyl acetate/hexane to give 13.44 g (77.7%) of the product as a white solid: $^1$H NMR ($CDCl_3$) d 0.87–0.97 (m, 6H), 1.16–1.32 (m, 4H), 1.34–1.48 (m, 4H), 1.50–1.69 (m, 4H), 1.86–1.96 (m, 1H), 2.88 (d, J=13.0 Hz, 1H), 3.00 (d, J=13.0 Hz, 1H), 3.85 (s, 3H), 4.00 (s, 1H), 4.48 (s, 1H), 6.52 (dd, J=9.9 Hz, 2.4 Hz, 1H), 6.94 (d, J=9 Hz, 2H), 7.13 (dt, J=8.4 Hz, 2.4 Hz, 1H), 7.38 (d, J=8.7 Hz, 2H), 7.82 (dd, J=8.7 Hz, 5.7 Hz, 1H).

Step 8. Preparation of enantiomerically-enriched tetrahydrobenzothiepine-1,1-dioxide (4R,5R)

To a stirred solution of 13.44 g (31.07 mmol) of enantiomerically-enriched tetrahydrobenzothiepine-1-oxide (obtained from Step 7) in 150 mL of methylene chloride was added 9.46 g of 68% m-chloroperoxybenzoic acid (37.28 mmol, Sigma) at 0° C. After stirring at 0° C. for 2 hours, the mixture was allowed to warm up to room temperature and stirred for 4 hours. 50 mL of saturated $Na_2SO_3$ was added into the mixture and stirred for 30 minutes. The solution was then neutralized with 50 mL of saturated $NaHCO_3$ solution. The methylene chloride layer was separated, dried over $MgSO_4$, and concentrated in vacuo to give 13.00 g (97.5%) of the enantiomerically-enriched tetrahydrobenzothiepine-1, 1-dioxide (4R,5R) as a light yellow solid: $^1$H NMR ($CDCl_3$) d 0.89–0.95 (m, 6H), 1.09–1.42 (m, 12H), 2.16–2.26 (m, 1H), 3.14 (q, J=15.6 Hz, 1H), 3.87 (s, 3H), 4.18 (s, 1H), 5.48 (s, 1H), 6.54 (dd, J=10.2 Hz, 2.4 Hz, 1H), 6.96–7.07 (m, 3H), 7.40 (d, J=8.1 Hz, 2H), 8.11 (dd, J=8.6 Hz, 5.9 Hz, 1H).

Step 9. Preparation of enantiomerically-enriched 7-(dimethylamino)tetrahydrobenzothiepine-1,1-dioxide (4R,5R)

To a solution of 13.00 g (28.98 mmol) of enantiomerically-enriched tetrahydrobenzothiepine-1,1-dioxide (obtained from Step 8) in 73 mL of dimethylamine (2.0 M in THF, 146 mmol) in a Parr Reactor was added ca. 20 mL of neat dimethylamine. The mixture was sealed and stirred at 110° C. overnight, and cooled to ambient temperature. The excess dimethylamine was evaporated. The crude oil was dissolved in 200 mL of ethyl acetate and washed with 100 mL of water, dried over $MgSO_4$ and concentrated in vacuo. Purification on a silica gel column (Waters Prep 500) using 20% ethyl acetate/hexane gave 12.43 g (90.5%) of the enantiomerically-enriched 7-(dimethylamino)tetrahydrobenzothiepine-1,1-dioxide (4R,5R) as a colorless solid: $^1H$ NMR (CDCl$_3$) d 0.87–0.93 (m, 6H), 1.10–1.68 (m, 12H), 2.17–2.25 (m, 1H), 2.81 (s, 6H), 2.99 (d, J=15.3 Hz, 1H), 3.15 (d, J=15.3 Hz, 1H), 3.84 (s, 3H), 4.11 (d, J=7.5 Hz, 1H), 5.49 (s, 1H), 5.99 (d, J=2.4 Hz, 1H), 6.51 (dd, J=8.7 Hz, 2.4 Hz, 1H), 6.94 (d, J=8.7 Hz, 2H), 7.42 (d, J=8.4 Hz, 2H), 7.90 (d, J=8.7 Hz, 201H). The product was determined to have 78% e.e. by chiral HPLC on a Chiralpak AD column using 5% ethanol/hexane as the eluent. Recrystallization of this solid from ethyl acetate/hexane gave 1.70 g of the racemic product. The remaining solution was concentrated and recrystallized to give 9.8 g of colorless solid. Enantiomeric excess of this solid was determined by chiral HPLC on a Chiralpak AD column using 5% ethanol/hexane as the eluent. It showed to have 96% e.e with the first eluting peak as the major product.

Step 10: Demethylation of 5-(4'-methoxyphenyl)-7-(dimethylamino)tetrahydrobenzothiepine-1,1-dioxide (4R, 5R)

To a solution of 47 g (99 mmol) of enantiomeric-enriched (dimethylamino)tetrahydrobenzothiepine-1,1-dioxide (obtained from Step 9) in 500 mL of methylene chloride at −10° C. was added dropwise a solution of boron tribromide (297 mL, 1M in methylene chloride, 297 mmol), and the resulting solution was stirred cold (−5° C. to 0° C.) for 1 hour or until the reaction was complete. The reaction was cooled in an acetone-dry ice bath at −10° C., and slowly quenched with 300 mL of water. The mixture was warmed to 10° C., and further diluted with 300 mL of saturated sodium bicarbonate solution to neutralize the mixture. The aqueous layer was separated and extracted with 300 mL of methylene chloride, and the combined extracts were washed with 200 mL of water, brine, dried over $MgSO_4$ and concentrated in vacuo. The residue was dissolved in 500 mL of ethyl acetate and stirred with 50 mL of glacial acetic acid for 30 minutes at ambient temperature. The mixture was washed twice with 200 mL of water, 200 mL of brine, dried over $MgSO_4$ and concentrated in vacuo to give the crude 4-hydroxyphenyl intermediate. The solid residue was recrystallized from methylene chloride to give 37.5 g (82%) of the desired (4R,5R)-5-(4'-hydoxyphenyl)-7-(dimethylamino)tetrahydrobenzothiepine-1,1-dioxide as a white solid: $^1H$ NMR (CDCl$_3$) d 0.84–0.97 (m, 6H), 1.1–1.5 (m, 10H), 1.57–1.72 (m, 1H), 2.14–2.28 (m, 1H), 2.83 (s, 6H), 3.00 (d, J=15.3 Hz, 1H), 3.16 (d, J=15.3 Hz, 1H), 4.11 (s, 2H), 5.48 (s, 1H), 6.02 (d, J=2.4 Hz, 1H), 6.55 (dd, J=9, 2.4 Hz, 1H), 6.88 (d, 8,7 Hz, 2H), 7.38 (d, J=8.7 Hz, 2H), 7.91 (d, J=9 Hz, 2H).

Step 11: Preparation of enantiomerically-enriched chlorobenzyl intermediate

Treat a solution of enantiomerically-enriched (4R,5R)-5-(4'-hydoxyphenyl)-7-(dimethylamino)tetrahydrobenzothiepine-1,1-dioxide (5.0 g, 10.9 mmol, obtained from Step 10) in acetone (100 mL) at 25° C. under $N_2$ with powdered $K_2CO_3$ (2.3 g, 16.3 mmol, 1.5 eq.) and a,a'-dichloro-p-xylene (6.7 g, 38.1 mmol, 3.5 eq.). Stir the resulting solution at 65° C. for about 48 hours. Cool the reaction mixture to 25° C. and concentrate to ⅕ of original volume. Dissolve the residue in EtOAc (150 mL) and wash with water (2×150 mL). Extract the aqueous layer with EtOAc (2×150 mL) and wash the combined organic extracts with saturated aqueous NaCl (2×150 mL). Dry the combined extracts with $MgSO_4$ and concentrate in vacuo to provide the crude product. Purification by flash chromatography (5.4×45 cm silica, 25–40% EtOAc/hexane) will afford the enantiomerically-enriched chlorobenzyl intermediate.

Step 12: Preparation of enantiomerically-enriched (4R,5R)-1-[[4-[[4-[3,3-Dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane chloride (XXVII)

Treat a solution of the enantiomerically-enriched chlorobenzyl intermediate (4.6 g, 7.7 mmol, obtained from above in Step 11) in acetonitrile (100 mL) at 25° C. under $N_2$ with diazabicyclo[2.2.2]-octane (DABCO, 0.95 g, 8.5 mmol, 1.1 eq.) and stir at 35° C. for 2 hours. Collect the precipitated solid and wash with $CH_3CN$. Recrystallization from $CH_3OH/Et_2O$ will give the desired title compound (XXVII).

The examples herein can be repeated with similar success by substituting the generically or specifically described reactants and/or operating conditions of this invention for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method of preparing an enantiomerically-enriched tetrahydrobenzothiepine-1-oxide having a formula (I):

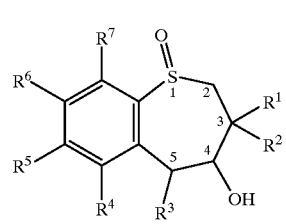

(I)

wherein:
$R^1$ and $R^2$ are independently selected from the group consisting of H, alkyl, alkenyl, alkynyl, cycloalkyl, aryl, and heteroaryl;

$R^3$ is selected from the group consisting of H, alkyl, alkenyl, alkynyl, aryl, cycloalkyl, heterocycle, quaternary heterocycle, $OR^{24}$, $SR^{15}$, $S(O)R^{15}$, $SO_2R^{15}$, and $SO_3R^{15}$;

$R^{24}$ is selected from the group consisting of alkyl, alkenyl, alkynyl, cycloalkyl, aryl, acyl, heterocycle, ammoniumalkyl, alkylammoniumalkyl, and arylalkyl;

$R^{15}$ is independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboalkylamino, heteroarylalkyl, heterocyclealkyl, and alkylammoniumalkyl; and $R^4$, $R^5$, $R^6$, $R^7$ are independently selected from the group consisting of H, alkyl, alkenyl, alkynyl, cycloalkyl, aryl, heteroaryl, halo, alkoxy, aryloxy, —$NO_2$, and —$NR^9R^{10}$;

$R^9$ and $R^{10}$ are independently selected from the group consisting of H, alkyl, alkenyl, alkynyl, cycloalkyl, aryl, heteroaryl, butoxycarbonyl, and carbobenzyloxy;

$R^3$ and the hydroxyl at the 4-position of the enantiomerically-enriched tetrahydrobenzothiepine-1-oxide are in a syn-conformation with respect to each other;

the sulfur at the 1-position of the seven-member ring and the carbons at the 4-position and the 5-position of the seven member ring are chiral centers;

wherein the method comprises:

(a) oxidizing an aryl-3-hydroxypropylsulfide having a formula (IV):

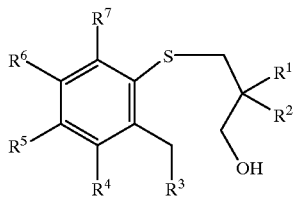

(IV)

wherein $R^1$, $R^2$, $R^3$, $R^4$, $R^5$, $R^6$, and $R^7$ are as described above to produce an enantiomerically-enriched aryl-3-hydroxypropylsulfoxide having a formula (III):

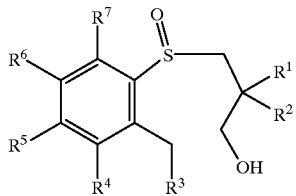

(III)

wherein $R^1$, $R^2$, $R^3$, $R^4$, $R^5$, $R^6$, and $R^7$ are as described above;

(b) oxidizing the 3-hydroxyl group of the enantiomerically-enriched aryl-3-hydroxypropyl-sulfoxide of formula (111) to produce an enantiomerically-enriched aryl-3-propanalsulfoxide having a formula (11):

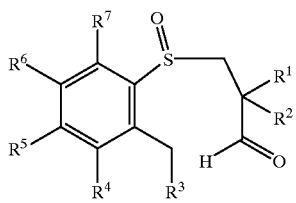

(II)

wherein $R^1$, $R^2$, $R^3$, $R^4$, $R^5$, $R^6$, and $R^7$ are as described above; and (c) cyclizing the enantiomerically-enriched aryl-3-propanalsulfoxide of formula (II) to form the enantiomerically-enriched tetrahydrobenzothiepine-1-oxide of formula (I).

2. The method of claim 1 wherein said oxidizing step (a) comprises oxidizing in the presence of a chiral oxaziridine.

3. The method of claim 2 wherein the chiral oxaziridine is (1)-(−)-(8,8-dichloro-10-camphor-sulfonyl)oxaziridine.

4. The method of claim 2 wherein the chiral oxaziridine is (1S)-(+)-(8,8-dichloro-10-camphor-sulfonyl)oxaziridine.

5. The method of claim 2 wherein said oxidizing step (a) further comprises oxidizing in the presence of a titanium (IV) alcoholate and a dialkyltartrate.

6. The method of claim 4 wherein said oxidizing step (a) further comprises oxidizing in the presence of a hydroperoxide compound having a formula (V):

$R^8$—O—O—H     (V)

wherein $R^8$ is a moiety selected from the group consisting of H, alkyl, carboalkyl, benzyl, benzoyl, and cumyl.

7. The method of claim 6 wherein $R^8$ is cumyl.

8. The method of claim 6 wherein $R^8$ is tert-butyl.

9. The method of claim 5 wherein said titanium (IV) alcoholate comprises titanium (IV) isopropoxide and said dialkyltartrate comprises diethyl-D-tartrate.

10. The method of claim 9 wherein said oxidizing step (a) further comprises oxidizing in the presence of a hydroperoxide compound having a formula (V):

$R^8$—O—O—H     (V)

wherein $R^8$ is a moiety selected from the group consisting of H, alkyl, carboalkyl, benzyl, benzoyl, and cumyl.

11. The method of claim 10 wherein $R^8$ is cumyl.

12. The method of claim 10 wherein $R^8$ is tert-butyl.

13. The method of claim 1 said oxidizing step (a) further comprises oxidizing in the presence of a chiral (salen)metal complex and an oxidizing agent.

14. The method of claim 13 wherein the oxidizing agent is iodobenzene diacetate.

15. The method of claim 14 wherein the chiral (salen) metal complex is (S,S)-(+)-N,N′-bis(3,5-di-tert-butylsalicyclidene)-1,2-cyclohexanediaminomanganese (III) chloride.

16. The method of claim 1 wherein the oxidation of the enantiomerically-enriched aryl-3-hydroxypropylsulfoxide of formula (III) in step (b) is performed in the presence of a sulfur trioxide pyridine complex.

17. The method of claim 1 wherein the oxidation of the enantiomerically-enriched aryl-3-hydroxypropyl sulfoxide of formula (III) in said oxidizing step (b) is performed in the presence of a pyridinium-chromium complex.

18. The method of claim 1 wherein the cyclizing of step (c) is performed in the presence of a base.

19. The method of claim 18 wherein the base is potassium tert-butoxide.

20. The method of claim 1 wherein $R^1$ and $R_2$ are moieties independently selected from the group consisting of ethyl and n-butyl.

21. The method of claim 1 wherein $R^1$ and $R_2$ are both n-butyl.

22. The method of claim 1 wherein $R^3$ has a formula (VI):

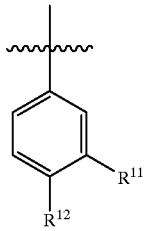

(VI)

wherein:

$R^{11}$ and $R^{12}$ are independently selected from the group consisting of H, alkoxy, —$NO_2$, —$NR^9R^{10}$, and —$OR^{10}$; and $R^9$ and $R^{10}$ are independently selected from the group consisting of H, alkyl, alkenyl, alkynyl, cycloalkyl, aryl, heteroaryl, butoxycarbonyl, and carbobenzyloxy.

23. The method of claim 22 wherein $R^1$ and $R_2$ are moieties independently selected from the group consisting of ethyl and n-butyl.

24. The method of claim 22 wherein $R^1$ and $R_2$ are both n-butyl.

25. The method of claim 24 wherein $R^{11}$ is H and $R^{12}$ is methoxy.

26. The method of claim 1 wherein $R^1$ and $R^2$ are both n-butyl; and wherein $R^3$ comprises a structure of formula (IIa):

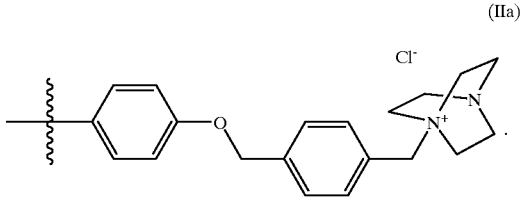

(IIa)

27. The method of claim 1 wherein $R^4$, $R^5$, $R^6$, and $R^7$ are moieties independently selected from the group consisting of H, —$NO_2$, and —$NR^9R^{10}$.

28. The method of claim 27 wherein $R^4$, $R^6$, and $R^7$ are each H and $R^5$ is a moiety selected from the group consisting of —$NO_2$ and —$NR^9R^{10}$.

29. The method of claim 22 wherein $R^4$, $R^5$, $R^6$, and $R^7$ are moieties independently selected from the group consisting of H, —$NO_2$, and —$NR^9R^{10}$.

30. The method of claim 29 wherein $R^4$, $R^6$, and $R^7$ are each H and $R^5$ is moiety selected from the group consisting of —$NO_2$ and —$NR^9R^{10}$.

31. The method of claim 29 wherein $R^5$ is dimethylamino.

32. The method of claim 31 wherein $R^{11}$, is H and $R^{12}$ is methoxy.

33. The method of claim 1 wherein $R^4$, $R^5$, $R^6$, and $R^7$ are moieties independently selected from the group consisting of H, —$NO_2$, and —$NR^9R^{10}$; wherein $R^5$ is dimethylamino; and wherein $R^3$ comprises a structure of formula (IIa):

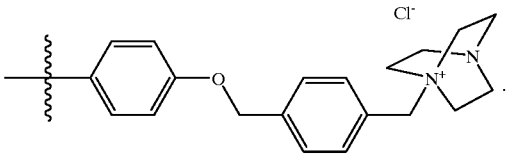

(IIa)

34. A method of preparing an enantiomerically-enriched tetrahydrobenzothiepine-1-oxide having the formula (I):

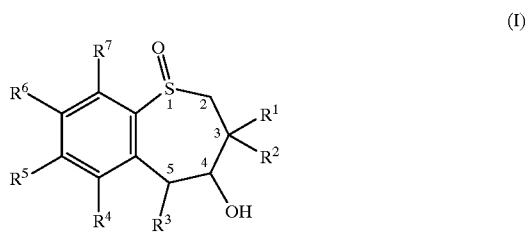

(I)

wherein:

(1) $R^1$ and $R^2$ are independently selected from the group consisting of H, alkyl, alkenyl, alkynyl, cycloalkyl, aryl, and heteroaryl;

(2) $R^3$ is member selected from a first group consisting of H, alkyl, alkenyl, alkynyl, aryl, cycloalkyl, heterocycle, quaternary heterocycle, $OR^{24}$, $SR^{15}$, $S(O)R^{15}$, $SO_2R^{15}$, and $SO_3R^{15}$, wherein said alkyl, alkenyl, alkynyl, aryl, cycloalkyl, heterocycle, quaternary heterocycle, and quaternary heteroaryl of said first group are independently further substituted with at least one member selected from a second group consisting of H, alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $OR^{19}$, $NR^{19}R^{20}$, $SR^{19}$, $S(O)R^{19}$, $SO_2R^{19}$, $SO_3R^{19}$, $NR^{19}OR^{20}$, $NR^{19}NR^{20}R^{21}$, $NO_2$, $CO_2R^{19}$, CN, OM, $SO_2OM$, $SO_2NR^{19}R^{20}$, $C(O)NR^{19}NR^{20}$, C(O)OM, $COR^{19}$, $P(O)R^{19}R^{20}$, $P^+R^{19}R^{20}R^{21}A^-$, $P(OR^{19})OR^{20}$, $S^+R^{19}R^{20}A^-$, and $N^+R^{15}R^{17}R^{18}A^-$, wherein $A^-$ is a pharmaceutically acceptable anion and M is a pharmaceutically acceptable cation;

wherein said alkyl, alkenyl, alkynyl, polyalkyl, polyether, aryl, haloalkyl, cycloalkyl, and heterocycle of said second group are independently further substituted with at least one substituent selected from a third group consisting of H, $OR^{13}$, $NR^{13}R^{14}$, $SR^{13}$, $S(O)R^{13}$, $SO_2R^{13}$, $SO_3R^{13}$, $CO_2R^{13}$, CN, oxo, $CONR^{13}R^{14}$, $N^+R^{13}R^{14}R^{15}A^-$, alkyl, alkenyl, alkynyl, aryl, cycloalkyl, heterocycle, arylalkyl, quaternary heterocycle, quaternary heteroaryl, P(O)$R^{13}R^{14}$, $P^+R^{13}R^{14}R^{15}A^-$, and $P(O)(OR^{13})OR^{14}$, and wherein said alkyl, alkenyl, alkynyl, polyalkyl, polyether, aryl, haloalkyl, cycloalkyl, and heterocycle of said third group have at least one carbon replaced by C, O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, or phenylene;

$R^{19}$, $R^{20}$, and $R^{21}$ are independently substituted with at least one member selected from a fourth group consisting of hydrogen, alkyl, alkenyl, alkynyl, polyalkyl, aryl, arylalkyl, cycloalkyl, heterocycle, heteroaryl, quaternary heterocycle, quaternary heteroaryl, polyether, alkylarylalkyl, alkylheteroarylalkyl, alkylheterocyclealkyl, heterocyclealkyl, heteroarylalkyl, quaternary heterocyclealkyl, alkylammoniumalkyl, carboxyalkylaminocarbonylalkyl, and quaternary heteroarylalkyl, wherein said alkyl, alkenyl, alkynyl, arylalkyl, heterocycle, and polyalkyl of said fourth group have at least one carbon replaced by C, O, $NR^{15}$, $N^+R^{15}R^{16}A^-$, S, SO, $SO_2$, $S^+R^{15}A^-$, $PR^{15}$, $P^+R^{15}R^{16}A^-$, $P(O)R^{15}$, phenylene, carbohydrate, amino acid, peptide, or polypeptide, and $R^{19}$, $R^{20}$, and $R^{21}$ are independently further substituted with at least one member selected from a fifth group consisting of hydrogen, hydroxy, amino, sulfo, carboxy, sulfoalkyl, carboxyalkyl, sulfoalkyl, alkyl, heterocycle, heteroaryl, quaternary heterocyclealkyl, quaternary heteroarylalkyl, guanidinyl, quaternary heterocycle, quaternary heteroaryl, $OR^{15}$, $NR^{15}R^{16}$, $N^+R^{15}R^{17}R^{18}A^-$, $SR^{15}$, $S(O)R^{15}$, $SO_2R^{15}$, $SO_3R^{15}$, oxo, $CO_2R^{15}$, CN, halogen, $CONR^{15}R^{16}$, $SO_2OM$, $SO_2NR^{15}R^{16}$, $PO(OR^{22})OR^{23}$, $P^+R^{15}R^{16}R^{17}A^-$, $S^+R^{15}R^{16}A^-$, and C(O)OM, wherein $R^{22}$ and $R^{23}$ are independently selected from the group consisting of $R^{15}$ and M, or $R^{20}$ and $R^{21}$, together with the nitrogen atom to which they are attached, form a cyclic ring;

$R^{24}$ is selected from the group consisting of alkyl, alkenyl, alkynyl, cycloalkyl, aryl, acyl, heterocycle, ammoniumalkyl, alkylammoniumalkyl, and arylalkyl;

$R^{13}$ and $R^{14}$ are independently selected from the group consisting of hydrogen and alkyl;

$R^{15}$ and $R^{16}$ are independently selected from the group consisting of H, alkyl, alkenyl, alkynyl, cycloalkyl, aryl, acyl, heterocycle, ammoniumalkyl, arylalkyl, carboxyalkyl, carboxyheteroaryl, carboxyheterocycle, carboalkoxyalkyl, carboalkylamino, heteroarylalkyl, heterocyclealkyl, and alkylammoniumalkyl; and $R^{17}$ and $R^{18}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^{15}$, $NR^{15}R^{16}$, $SR^{15}$, $S(O)R^{15}$, $SO_2R^{15}$, $SO_3R^{15}$, $CO_3R^{15}$, CN, halogen, oxo, and $CONR^{15}R^{16}$, wherein $R^{15}$ and $R^{16}$ are as defined above, or $R^{17}$ and $R^{18}$ together with the nitrogen or carbon atom to which they are attached form a cyclic ring;

(3) $R^4$, $R^5$, $R^6$, $R^7$ are independently selected from a sixth group consisting of H, alkyl, alkenyl, alkynyl, cycloalkyl, aryl, heteroaryl, halo, alkoxy, aryloxy, $—NO_2$, and $—NR^9R^{10}$;

$R^9$ and $R^{10}$ are independently selected from the group consisting of H, alkyl, alkenyl, alkynyl, cycloalkyl, aryl, heteroaryl, butoxycarbonyl, and carbobenzyloxy;

(4) $R^3$ and the hydroxyl at the 4-position of the enantiomerically-enriched tetrahydrobenzothiepine-1-oxide are in a syn-conformation with respect to each other;

said alkyl, alkenyl, alkynyl, cycloalkyl, aryl, heteroaryl, alkoxy, and aryloxy of said sixth dependently further substituted with at least one substituent selected from the group consisting of H, alkyl, alkenyl, alkynyl, cycloalkyl, aryl, heteroaryl, alkoxy, aryloxy, $—NO_2$, and halo; and the position of the seven-member ring and the carbons at the 4-position and the 5-position of the seven member ring are chiral centers; method comprises:

(a) oxidizing an aryl-3-hydroxypropylsulfide having a formula (IV):

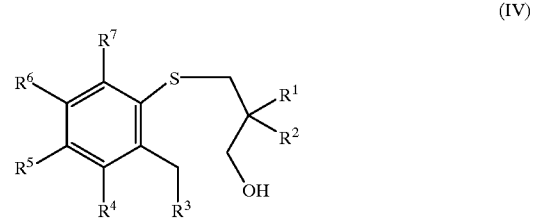

(IV)

wherein $R^1$, $R^2$, $R^3$, $R^4$, $R^5$, $R^6$, and $R^7$ are as described above, to produce an enriched aryl-3-hydroxypropylsulfoxide having a formula (III):

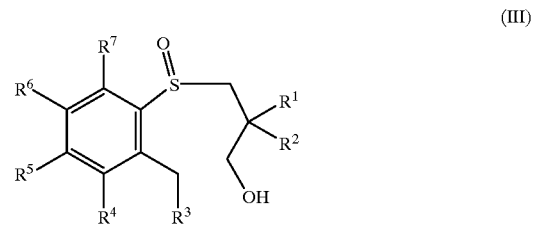

(III)

wherein $R^1$, $R^2$, $R^3$, $R^4$, $R^5$, $R^6$, and $R^7$ are as described above, and the sulfur is an enantiomerically-enriched chiral center;

(b) oxidizing the 3-hydroxyl group of he enantiomerically-enriched aryl-3-hydroxypropyl-sulfoxide to produce an enantiomerically-enriched aryl-3-propanalsulfoxide having a formula (II):

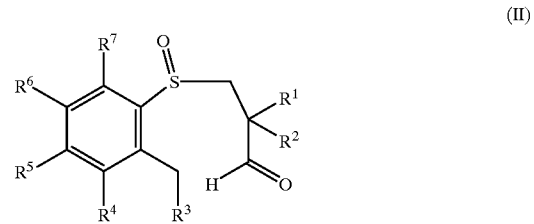

(II)

wherein $R^1$, $R^2$, $R^3$, $R^4$, $R^5$, $R^6$ and $R^7$ are as described the an enantiomerically-enriched chiral center; and (c) cyclizing the enantiomerically-enrich d aryl-3-propanalsulfoxide to form the enantiomerically-enriched tetrahydrobenzothiepine-1-oxide of said formula (I).

35. The method of claim 34 wherein said oxidizing step (a) comprises oxidizing in the presence of a chiral oxaziridine.

36. The method of claim 35 wherein said chiral oxaziridine is (1R)-(−)-(8,8-dichloro-10-camphor-sulfonyl) oxaziridine.

37. The method of claim 35 wherein said chiral oxaziridine comprises (1S)-(+)(8,8-dichloro-10-camphor-sulfonyl) oxaziridine.

38. The method of claim 35 wherein aid oxidizing step (a) comprises oxidizing in the presence of a titanium (IV) alcoholate and a dialkyltartrate.

39. The method of claim 37 wherein said oxidizing step (a) comprises oxidizing in the presence of a hydroperoxide compound having a formula (V):

$$R^8-O-O-H \quad (V)$$

wherein $R^8$ is a moiety selected from the group consisting of H, alkyl, carboalkyl, benzyl, benzoyl, and cumyl.

40. The method of claim 39 wherein $R^8$ is cumyl.

41. The method of claim 39 wherein $R^8$ is tert-butyl.

42. The method of claim 38 wherein said titanium alcoholate comprises titanium (IV) isopropoxide and said dialkyltartrate comprises diethyl-D-tartrate.

43. The method of claim 42 wherein said oxidizing step (a) further comprises oxidizing in the presence of a hydroperoxide compound having a formula (V):

$$R^8-O-O-H \quad (V)$$

wherein $R^8$ is a moiety selected from the group consisting of H, alkyl, carboalkyl, benzyl, benzoyl, and cumyl.

44. The method of claim 43 wherein $R^8$ is cumyl.

45. The method of claim 43 wherein $R^8$ is tert-butyl.

46. The method of claim 34 wherein said oxidizing step (a) further comprises oxidizing in the presence of a chiral (salen)metal complex and an oxidizing agent.

47. The method of claim 46 wherein said oxidizing agent comprises iodobenzene diacetate.

48. The method of claim 47 wherein the chiral (salen) metal complex comprises (S,S)-(+)-N,N'-bis(3,5-di-tert-butylsalicyclidene)-1,2-cyclohexanediaminomanganese (III) chloride.

49. The method of claim 34 wherein the oxidation of the enantiomerically-enriched aryl-3-hydroxypropylsulfoxide of said formula (III) in said step (b) is performed in the presence of sulfur trioxide pyridine complex.

50. The method of claim 34 wherein the oxidation of the enantiomerically-enriched aryl-3-hydroxypropyl-sulfoxide of said formula (III) in said step (b) is performed in the presence of a pyridinium-chromium complex.

51. The method of claim 34 wherein said cyclizing of step (c) is performed in the presence of a base.

52. The method of claim 51 wherein said base is potassium tert-butoxide.

53. The method of claim 34 wherein said $R^1$ and said $R^2$ are moieties independently selected from the group consisting of ethyl and n-butyl.

54. The method of claim 34 wherein said $R^1$ and said $R^2$ are both n-butyl.

55. The method of claim 34 wherein said $R^3$ has a formula (VI):

(VI)

wherein:

$R^{11}$ and $R^{12}$ are independently selected from the group consisting of H, alkoxy, —$NO_2$, —$NR^9R^{10}$, and —$OR^{10}$; and $R^9$ and $R^{10}$ are independently selected from the group consisting of H, alkyl, alkenyl, alkynyl, cycloalkyl, aryl, heteroaryl, butoxycarbonyl, and carbobenzyloxy, wherein said aryl and heteroaryl are substituted with at least one member selected from the group consisting of H, alkyl, alkenyl, alkynyl, cycloalkyl, aryl, heteroaryl, alkoxy, aryloxy, and halo.

56. The method of claim 55 wherein said $R^1$ and said $R^2$ are moieties independently selected from the group consisting of ethyl and n-butyl.

57. The method of claim 55 wherein said $R^1$ and said $R^2$ are both n-butyl.

58. The method of claim 57 wherein said $R^{11}$ is H and said $R^{12}$ is methoxy.

59. The method of claim 57 wherein said $R^3$ is a group having the structure of formula (IIa):

(IIa)

60. The method of claim 34 wherein $R^4$, $R^5$, $R^6$, and $R^7$ are moieties independently selected from the group consisting of H, —$NO_2$, and —$NR^9R^{10}$.

61. The method of claim 60 wherein said $R^4$, said $R^5$, said $R^6$, and said $R^7$ are each H and said $R^5$ is a moiety selected from the group consisting of —$NO_2$ and —$NR^9R^{10}$.

62. The method of claim 55 wherein said $R^4$, said $R^5$, said $R^6$, and said $R^7$ are moieties independently selected from the group consisting of H, —$NO_2$, and —$NR^9R^{10}$.

63. The method of claim 62 wherein said $R^4$, said $R^6$, and said $R^7$ are each H and said $R^5$ is a moiety selected from the group consisting of —$NO_2$, and —$NR^9R^{10}$.

64. The method of claim 62 wherein said $R^5$ is dimethylamino.

65. The method of claim 64 wherein said $R^{11}$ is H and said $R^{12}$ is methoxy.

66. The method of claim 64 wherein said $R^3$ is a group having the structure of formula (IIa):

(IIa)

* * * * *